(12) United States Patent
Iwasaki et al.

(10) Patent No.: US 6,730,803 B2
(45) Date of Patent: May 4, 2004

(54) SYNTHETIC INTERMEDIATE FOR EPOTHILONE DERIVATIVE AND PRODUCTION METHOD THEREOF

(75) Inventors: Mitsuhiro Iwasaki, Osaka (JP); Kiyoshi Sugi, Osaka (JP); Hideto Miyamoto, Osaka (JP); Nobushige Itaya, Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 22 days.

(21) Appl. No.: 10/260,946

(22) Filed: Sep. 30, 2002

(65) Prior Publication Data

US 2003/0144533 A1 Jul. 31, 2003

(30) Foreign Application Priority Data

| Sep. 28, 2001 | (JP) | 2001-304278 |
| Oct. 1, 2001 | (JP) | 2001-305854 |
| Oct. 2, 2001 | (JP) | 2001-306842 |
| Mar. 7, 2002 | (JP) | 2002-062022 |

(51) Int. Cl.[7] ............... C07C 255/00; C07D 319/06
(52) U.S. Cl. ............... 558/442; 558/354; 558/443; 549/369
(58) Field of Search ............... 549/369; 558/442, 558/443, 354

(56) References Cited

U.S. PATENT DOCUMENTS

2002/0156289 A1 10/2002 Georg et al.

FOREIGN PATENT DOCUMENTS

| WO | WO 03/014063 A2 | 2/2003 |
| WO | WO 03/014068 A1 | 2/2003 |

OTHER PUBLICATIONS

White et al., "Total Synthesis of Epothilone B, Epothilone D, and cis– and trans–9,10–Dehydroepothilone D," *J. Am. Chem. Soc., 123* (23), 5407–5413 (Nov. 23, 2001).

Bode et al., "Stereoselective Syntheses of Epopthilones A and B via Nitrile Oxide Cycloadditions and Related Studies," *J. Org. Chem., 66* (19), 6410–6424 (2001).

*Primary Examiner*—Amelia Owens
(74) *Attorney, Agent, or Firm*—Leydig, Voit & Mayer, Ltd.

(57) ABSTRACT

The β-keto ester compound, β-hydroxy acid compound and acetonide form of a 1,3-diol derivative of the formulas (I), (V) and (VIII)

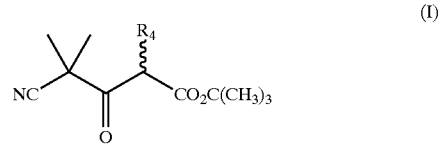

(I)

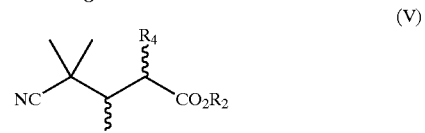

(V)

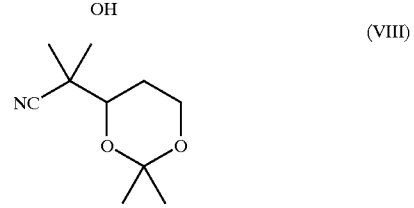

(VIII)

wherein each symbol is as defined in the specification, are useful as a synthetic intermediate for an epothilone derivative being developed as a pharmaceutical agent having an antitumor activity.

28 Claims, No Drawings

SYNTHETIC INTERMEDIATE FOR EPOTHILONE DERIVATIVE AND PRODUCTION METHOD THEREOF

TECHNICAL FIELD OF THE INVENTION

The present invention relates to a β-keto ester compound, a β-hydroxy acid compound and an acetonide form of a 1,3-diol derivative, which are useful as a synthetic intermediate for a pharmaceutical or agrichemical agent, and production methods thereof. The β-keto ester compound, the β-hydroxy acid compound and the acetonide form of a 1,3-diol derivative obtained by the present invention are useful as a synthetic intermediates for an epothilone derivative being developed as a pharmaceutical agent having antitumor activity.

BACKGROUND OF THE INVENTION

Epothilone is a substance produced by myxobacterium Sorangium cellulosum and is known to have high antitumor activity.

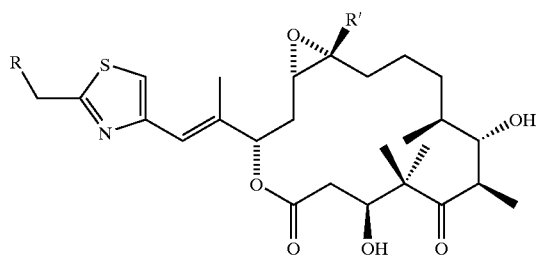

R = R' = H; Epothilone A
R = H, R' = Me; Epothilone B
R = OH, R' = H; Epothilone E
R = OH, R' = Me; Epothilone F

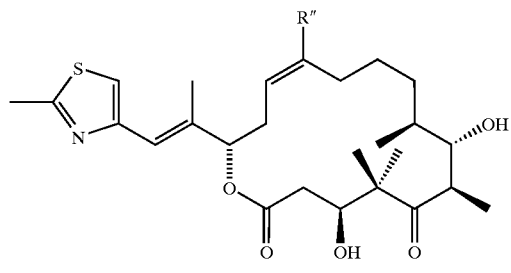

R'' = H; Epothilone C
R'' = Me; Epothilone D

In recent years, energetic studies of synthetic structural conversion in an effort to obtain an epothilone derivative showing higher performance are ongoing (general synthetic methods of epothilone are shown in J. Am. Chem. Soc. 2001, 123, 5407–5413 and publications quoted in this reference). For this purpose, various compounds useful as synthetic intermediates therefore have been studied.

The present inventors have investigated synthetic intermediates useful for the production of the above-mentioned epothilone derivative and noted the idea that the structure of a novel compound, tert-butyl 4-cyano-4-methyl-3-oxopentanoate, represented by the following formula

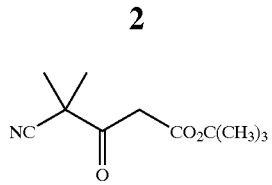

is useful as the above-mentioned synthetic intermediate. However, this novel compound is difficult to synthesize. That is, as a compound usable as a material for synthesizing the tert-butyl 4-cyano-4-methyl-3-oxopentanoate, a conventionally known 2-cyano-2,2-dimethylacetate represented by the following formula

wherein $R_1$ is alkyl group having 1 to 6 carbon atoms, is considered, but as is clear from the above-mentioned structural formula, 2-cyano-2,2-dimethylacetate has cyano group and ester residue as reaction sites in a single molecule. Thereby making selective production of the above-mentioned tert-butyl 4-cyano-4-methyl-3-oxopentanoate seems difficult.

However, if the above-mentioned tert-butyl 4-cyano-4-methyl-3-oxopentanoate can be synthesized from the above-mentioned 2-cyano-2,2-dimethylacetate, this compound is a desirable starting material because the compound can be economically prepared on a large-scale and in short steps. Thus, a development of a method for the production of the above-mentioned novel tert-butyl 4-cyano-4-methyl-3-oxopentanoate from 2-cyano-2,2-dimethylacetate has been investigated.

The compounds expected to be usable as synthetic intermediates for an epothilone derivative include a novel compound not published heretofore, which is tert-butyl 4-cyano-4-methyl-3-hydroxypentanoate represented by the following formula

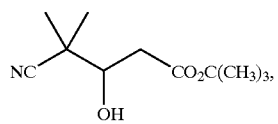

4-cyano-3-hydroxy-4-methylpentanoic acid represented by the following formula

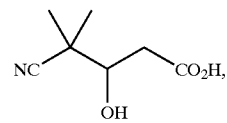

optically active 4-cyano-3-hydroxy-4-methylpentanoic acid represented by the following formula

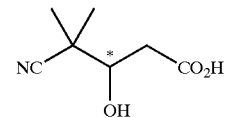

and optically active 4-cyano-3-hydroxy-4-methylpentanoate of the following formula

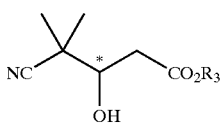

wherein $R_3$ is alkyl group having 1 to 6 carbon atoms. These synthetic intermediates are novel compounds, and convenient and economical production of these synthetic intermediates is expected to afford a large-scale synthesis of the final product, an epothilone derivative.

SUMMARY OF THE INVENTION

Accordingly, an object of the present invention is to provide a novel synthetic intermediate for the synthesis of an epothilone derivative useful as a pharmaceutical or agrichemical agent, particularly as an antitumor agent, and production methods thereof.

[1] A β-keto ester compound represented by the following formula

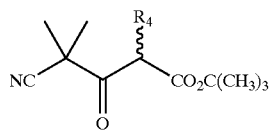

(I)

wherein $R_4$ is hydrogen atom or alkyl group having 1 to 6 carbon atoms, or an optically active form thereof.

[2] The compound of the above-mentioned [1], wherein $R_4$ is hydrogen atom, or an optically active form thereof.

[3] The compound of the above-mentioned [1], wherein $R_4$ is alkyl group having 1 to 6 carbon atoms, or an optically active form thereof.

[4] A production method of a β-keto ester compound of the above-mentioned [1], which comprises condensation of a 2-cyano-2,2-dimethylacetate represented by the following formula

(II)

wherein $R_1$ is alkyl group having 1 to 6 carbon atoms, with an alkyl ester represented by the following formula

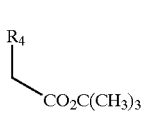

(III)

wherein $R_4$ is hydrogen atom or alkyl group having 1 to 6 carbon atoms, in the presence of a strong base.

[5] The production method of the above-mentioned [4], wherein $R_4$ is hydrogen atom.

[6] The production method of the above-mentioned [4], wherein $R_4$ is alkyl group having 1 to 6 carbon atoms.

[7] The production method of the above-mentioned [4], comprising adding lithium diisopropylamide as a strong base to a mixture of 2-cyano-2,2-dimethylacetate represented by the formula (II) and an alkyl ester represented by the formula (III).

[8] The production method of any of the above-mentioned [4]–[7], which comprises adding cyanoacetate of the following formula

(IV)

wherein $R_1$ is alkyl group having 1 to 6 carbon atoms, and dimethyl sulfate continuously or discontinuously to a sodium hydride-containing tetrahydrofuran solution to give 2-cyano-2,2-dimethylacetate of the formula (II), and condensation thereof with an alkyl ester of the formula (III).

[9] A β-hydroxy acid compound represented by the following formula

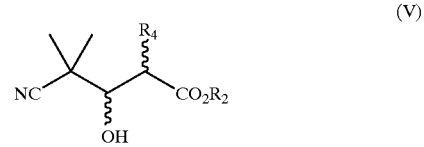

(V)

wherein $R_2$ is hydrogen atom or alkyl group having 1 to 6 carbon atoms, and $R_4$ is hydrogen atom or alkyl group having 1 to 6 carbon atoms, provided that when $R_4$ is alkyl group having 1 to 6 carbon atoms, $R_2$ should be tert-butyl group, an optically active form thereof or a salt thereof.

[10] The compound of the above-mentioned [9], wherein $R_4$ is hydrogen atom, an optically active form thereof or a salt thereof.

[11] The compound of the above-mentioned [9], wherein $R_4$ is alkyl group having 1 to 6 carbon atoms and $R_2$ is tert-butyl group, an optically active form thereof or a salt thereof.

[12] A production method of a β-hydroxy acid compound represented by the formula (V) of the above-mentioned [9], which comprises reducing a β-keto ester compound represented by the following formula

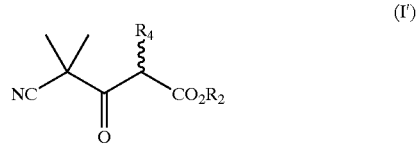

(I')

wherein $R_2$ is hydrogen atom or alkyl group having 1 to 6 carbon atoms, and $R_4$ is hydrogen atom or alkyl group having 1 to 6 carbon atoms, provided that when $R_4$ is alkyl group having 1 to 6 carbon atoms, $R_2$ should be tert-butyl group, or a salt thereof.

[13] The production method of the above-mentioned [12], wherein $R_4$ is alkyl group having 1 to 6 carbon atoms and $R_2$ is tert-butyl group.

[14] The production method of the above-mentioned [13], wherein the reduction is carried out using alkali borohydride and divalent metal chloride.

[15] The production method of the above-mentioned [12], wherein $R_4$ is hydrogen atom.

[16] The production method of the above-mentioned [15], wherein $R_2$ is alkyl group having 1 to 6 carbon atoms.

[17] The production method of the above-mentioned [16], wherein the alkyl group having 1 to 6 carbon atoms is tert-butyl group.

[18] The production method of any of the above-mentioned [15]–[17], wherein the reduction is carried out using sodium borohydride.

[19] The production method of the above-mentioned [14], wherein the β-keto ester compound of the formula (I'), wherein $R_2$ is alkyl group having 1 to 6 carbon atoms and $R_4$ is hydrogen atom, is reduced to give a β-hydroxy acid compound (V-4) represented by the following formula

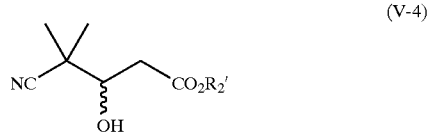
(V-4)

wherein $R_{2'}$ is alkyl group having 1 to 6 carbon atoms, which is a compound of the formula (V) wherein $R_2$ is alkyl group having 1 to 6 carbon atoms and $R_1$ is hydrogen atom, and the β-hydroxy acid compound (V-4) is subjected to alkali hydrolysis to give a β-hydroxy acid compound (V-5) of the following formula

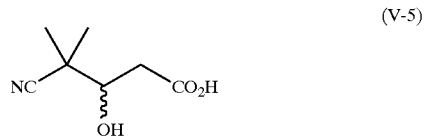
(V-5)

which is a compound of the formula (V) wherein $R_2$ and $R_4$ are hydrogen atoms.

[20] The production method of the above-mentioned [19], wherein the resulting β-hydroxy acid compound (V-5) is optically resolved to give a β-hydroxy acid compound (V-6) of the following formula

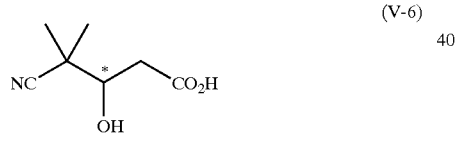
(V-6)

or a salt thereof, which is then esterified with an alkylating agent to give a β-hydroxy acid compound (V-7) represented by the following formula

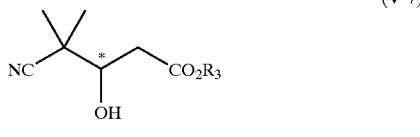
(V-7)

wherein $R_3$ is alkyl group having 1 to 6 carbon atoms, which is an optically active compound of the formula (V) wherein $R_2$ is alkyl group having 1 to 6 carbon atoms and $R_4$ is hydrogen atom.

[21] The production method of the above-mentioned [19] or [20], wherein each alkyl group having 1 to 6 carbon atoms is tert-butyl group.

[22] A production method of a β-hydroxy acid compound (V-6) represented by the following formula

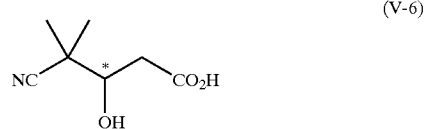
(V-6)

or a salt thereof, which is an optically active compound represented by the formula (V) of the above-mentioned [9], wherein $R_2$ and $R_4$ are hydrogen atoms, which comprises optical resolution of the β-hydroxy acid compound (V-5) represented by the following formula

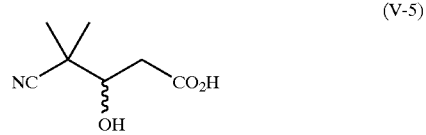
(V-5)

[23] The production method of the above-mentioned [22], wherein the β-hydroxy acid compound (V-5) is converted to a salt with an optically active amine compound and optically resolved.

[24] A production method of a β-hydroxy acid compound (V-7) represented by the following formula

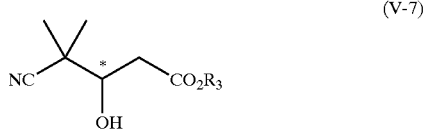
(V-7)

wherein $R_3$ is alkyl group having 1 to 6 carbon atoms, which is an optically active compound represented by the formula (V) of the above-mentioned [9], wherein $R_2$ is alkyl group having 1 to 6 carbon atoms and $R_4$ is hydrogen atom, which comprises esterification of a β-hydroxy acid compound (V-6) represented by the following formula

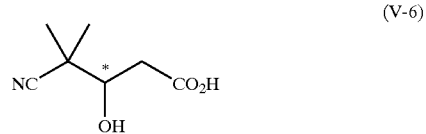
(V-6)

or a salt thereof with an alkylating agent.

[25] An acetonide form of a 1,3-diol derivative, which is represented by the following formula

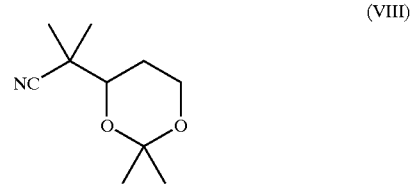
(VIII)

or an optically active form thereof.

[26] A production method of an acetonide form of a 1,3-diol derivative represented by the formula (VIII) of the above-mentioned [25], or an optically active form thereof, which comprises conversion of a 1,3-diol derivative represented by the following formula

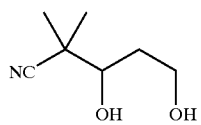

(VII)

or an optically active form thereof, to an acetonide form thereof.

[27] The production method of the above-mentioned [26], wherein the β-hydroxy acid compound of the following formula

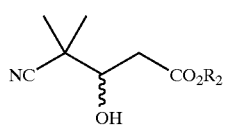

(V-2)

wherein $R_2$ is hydrogen atom or alkyl group having 1 to 6 carbon atoms, or an optically active form thereof is reduced to give a 1,3-diol derivative of the formula (VII) or an optically active form thereof, which is converted to an acetonide form.

[28] A production method of a 1,3-diol derivative represented by the following formula

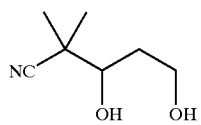

(VII)

or an optically active form thereof, which comprises reducing a β-hydroxy acid compound represented by the following formula

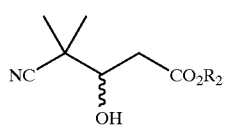

(V-2)

wherein $R_2$ is hydrogen atom or alkyl group having 1 to 6 carbon atoms, or an optically active form thereof.

DETAILED DESCRIPTION OF THE INVENTION

The definition of each symbol is explained in the following.

In the present specification, alkyl group having 1 to 6 carbon atoms may be linear or branched and is exemplified by methyl group, ethyl group, propyl group, isopropyl group, butyl group, isobutyl group, tert-butyl group, pentyl group and hexyl group. $R_1$ is preferably a group showing small steric hindrance, and is particularly preferably methyl group or ethyl group. $R_1$, $R_1$ and $R_3$ are preferably methyl group or ethyl group in view of easy availability.

To achieve the above-mentioned object, the present invention has the following characteristics.

β-keto Ester Compound (I) and Production Method Thereof

According to the production method of the present invention, as shown in the following Scheme 1, 2-cyano-2, 2-dimethylacetate represented by the formula (II) (hereinafter sometimes to be referred to as 2-cyano-2,2 dimethylacetate (II)) and an alkyl ester represented by the formula (III) (hereinafter sometimes to be referred to as alkyl ester (III)). Are condensed to give a novel β-keto ester compound represented by the formula (I) (hereinafter sometimes to be referred to as β-keto ester compound (I)).

[Scheme 1]

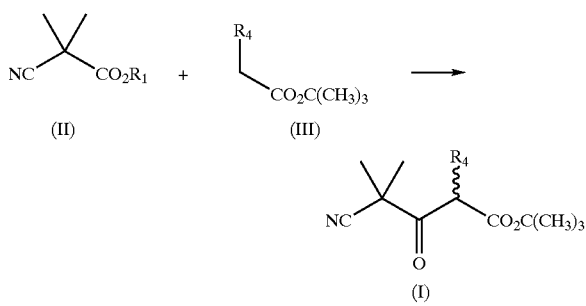

In the above-mentioned Scheme, $R_1$ is alkyl group having 1 to 6 carbon atoms and $R_4$ is hydrogen atom or alkyl group having 1 to 6 carbon atoms.

The production method of the present invention is realized by, for example, adding a strong base to a mixture of 2-cyano-2,2-dimethylacetate (II) and an alkyl ester (III). By carrying out the reaction by adding (e.g., dropwise addition) a strong base to the above-mentioned mixture, self condensation during anionizing the alkyl ester (III) can be suppressed, whereby 2-cyano-2,2-dimethylacetate (II) and an alkyl ester (III) are efficiently condensed. As a result, the above-mentioned β-keto ester compound (I) can be obtained in a high yield.

As the strong base to be used for the production method of the present invention, for example, lithium diisopropylamide (LDA), lithium hexamethyldisilazide, lithium isopropylcyclohexylamide, lithium dicyclohexylamide, lithium 2,2,6,6-tetramethylpiperidide, bromo magnesium diisopropylamide and the like can be used, of which LDA is preferable.

The solvent to be used for the preparation of a mixture of 2-cyano-2,2-dimethylacetate (II) and the above-mentioned alkyl ester (III) is subject to no particular limitation as long as it is inert to the above-mentioned condensation. Examples of the inert solvent include hydrocarbon solvents such as toluene, hexane and the like, ether solvents such as tetrahydrofuran (THF) and the like, and a mixed solvent thereof.

While the amount of the solvent to be used for preparing the mixture is not particularly limited, it is preferably a 0.5- to 10-fold weight, more preferably a 1- to 5-fold weight, relative to the total weight of the above-mentioned 2-cyano-2,2-dimethylacetate (II) and an alkyl ester (III). When the amount of use of the solvent is less than 0.5-fold amount relative to the amount of the reagent, the viscosity becomes high and the stirring may not be done sufficiently. When the amount of use of the solvent exceeds 10-fold amount of the reagent, it causes lower volume efficiency, which may not be economical.

The amount of the strong base to be used is not particularly limited and varies depending on the kind of the strong base. When, for example, LDA is used as a strong base, it is preferably used in an amount of 0.95–1.5 mol, more preferably 1.0–1.3 mol, per 1 mol of 2-cyano-2,2-dimethylacetate (II). When the amount of use of the LDA is less than 0.95 mol per 1 mol of 2-cyano-2,2-dimethylacetate (II), the reaction stops on the way to often reduce the yield. When the amount of use of the LDA exceeds 1.5 mol per 1 mol of 2-cyano-2,2-dimethylacetate (II), the amount of by-products tends to increase.

When LDA is used as a strong base, it may be used in the form of a solution upon dissolution of LDA in a solvent such as heptane, THF, hexane, toluene and the like. By forming such LDA solution, LDA becomes stable and easy to handle.

When LDA is used as a strong base, the temperature, at which the reaction is carried out, is preferably not higher than −50° C., more preferably from −100° C. to −50° C., particularly preferably around −70° C. (−80° C. to −60° C.), for the production of β-keto ester compound (I) in a higher yield. When the above-mentioned reaction is carried out at a temperature around −70° C. using LDA, self condensation of the above-mentioned alkyl ester (III) is further suppressed to permit extremely efficient progress of the reaction to quantitatively produce the objective β-keto ester compound (I) (yield: not less than 90%) using 1 equivalent amount each of an alkyl ester (III), 2-cyano-2,2-dimethylacetate (II) and LDA.

After the above-mentioned reaction shown in Scheme 1, the reaction mixture is warmed to a temperature of from −10° C. to room temperature, which is followed by addition of an acidic aqueous solution such as hydrochloric acid, acetic acid and the like, or addition of the reaction mixture into an acidic aqueous solution, to desirably make the solution near neutral. Thereafter, a generally used solvent, such as the above solvent used, or ethyl acetate or toluene is used to extract the resulting product.

Through the production method shown in Scheme 1 above, a β-keto ester compound (I) of the following formula

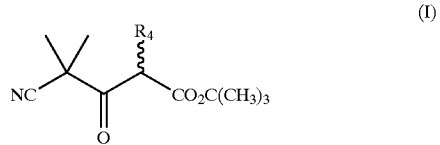

(I)

wherein $R_4$ is as defined above, can be produced in a yield of not less than 90%.
The following formula

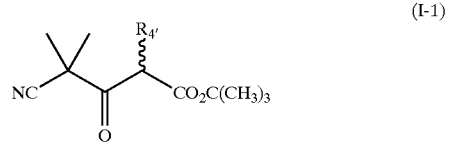

(I-1)

wherein $R_{4'}$ is alkyl group having 1 to 6 carbon atoms, which is the β-keto ester compound (I) wherein $R_4$ is alkyl group ($R_{4'}$) having 1 to 6 carbon atoms, includes two stereoisomers of the formula

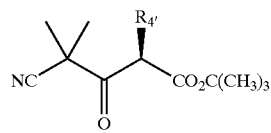

wherein $R_{4'}$ is alkyl group having 1 to 6 carbon atoms, and the formula

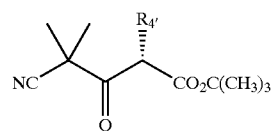

wherein $R_{4'}$ is alkyl group having 1 to 6 carbon atoms.

The β-keto ester compound (I) is a novel compound found for the first time by the present inventors. This compound is considered to be very useful as a synthetic intermediate for the production of an epothilone derivative being developed as a pharmaceutical agent having antitumor activity.

The aforementioned production method is only one example of a method for producing β-keto ester compound (I), and while the β-keto ester compound (I) of the present invention is not limited to those produced by the above-mentioned production method, it is preferably those produced by the above-mentioned production method.

The β-keto ester compound (I) of the present invention is easy to structurally enolize. The enol may not be susceptible to reduction, in which case the use of the β-keto ester compound (I) as a synthetic intermediate may cause inconvenience in the production of an β-hydroxy acid derivative (V). In the production method of the present invention, the proportion of enol form after treatment by the reaction shown in Scheme 1 is preferably reduced as much as possible to eliminate the possibility of the above-mentioned inconvenience.

When pH of the aqueous layer was changed from near neutral to 2 in the water washing treatment of the β-keto ester compound, it was found that pH 6.5–7.5 was optimal for suppressing the generation of enol, by observation of the shift of peaks in $^1$H-NMR.

The 2-cyano-2,2-dimethylacetate (II) and an alkyl ester (III) used as starting materials for the production method of β-keto ester compound (I) of the present invention are respectively obtained by conventionally known methods. It is also possible to use commercially available ones, but 2-cyano-2,2-dimethylacetate (II) is preferably produced by the following production method proposed by the present inventors.

Production Method of 2-cyano-2,2-dimethylacetate (II)

The 2-cyano-2,2-dimethylacetate (II) used as a starting material for the production method of β-keto ester compound (I) of the present invention is, as mentioned above, a conventionally known compound. The present inventors have found a production method shown in the following Scheme 2 that affords 2-cyano-2,2-dimethylacetate (II) in a high yield.

[Scheme 2]

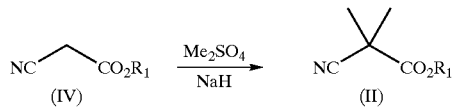

In this Scheme, $R_1$ is as defined above.

That is, in the present invention, a novel production method of 2-cyano-2,2-dimethylacetate (II) is also provided, which comprises continuously or discontinuously adding cyanoacetate represented by the above-mentioned formula (IV) (hereinafter to be sometimes referred to as cyanoacetate (IV)) and dimethyl sulfate to a sodium hydride (NaH)-containing THF solution.

In the above-mentioned production method, the use of NaH as a base permits a quantitative reaction as compared to the use of other bases, because it produces less contaminant. Furthermore, the use of THF as a solvent suppresses mixing of the resulting product in a distillation solvent during concentration of the reaction mixture after completion of the reaction, which in turn leads to a higher yield as compared to the use of other solvents. When $R_1$ is ethyl group (when ethyl cyanoacetate is used as cyanoacetate (IV)), mixing of the product in a distillation solvent during the above-mentioned concentration of the reaction mixture can be preferably suppressed further.

Sodium hydride is generally used as a dispersion in a 60% mineral oil. The amount of sodium hydride to be used is generally 2–3 mol, preferably 2.1–2.5 mol, per 1 mol of cyanoacetate (IV). The amount of THF to be used is generally 2–6 parts by weight, preferably 3–5 parts by weight, per 1 part by weight of ethyl cyanoacetate.

In the production method of the 2-cyano-2,2-dimethylacetate (II), cyanoacetate (IV) and dimethyl sulfate may be added continuously or discontinuously to an NaH-containing THF solution. It is preferable to add them in such a manner as to make the amount of hydrogen produced during the reaction below excess and to facilitate control of heat generation in the course of the reaction. The proportions of cyanoacetate (IV) and dimethyl sulfate to be added to an NaH-containing THF solution can be made to be almost the same as the proportions of cyanoacetate (IV) and dimethyl sulfate used for the reaction. When they are added continuously, the entire amount of cyanoacetate (IV) and dimethyl sulfate to be used for the reaction is respectively added continuously. When they are added discontinuously, the entire amount of cyanoacetate (IV) and dimethyl sulfate to be used for the reaction is divided in plural portions, and added discontinuously. In the latter case, the number of division of cyanoacetate (IV) is preferably almost the same as that of dimethyl sulfate. The proportions of cyanoacetate (IV) and dimethyl sulfate to be added to the NaH-containing THF solution can be made almost the same as the proportions of the cyanoacetate (IV) and dimethyl sulfate to be used for the reaction. This number of division varies depending on the scale of the reaction, and is free of any particular limitation as long as the reaction heat can be removed and the reaction temperature range to be mentioned later can be maintained. Where necessary, cyanoacetate (IV) and dimethyl sulfate may be mixed for dropwise addition.

The molar ratio of the cyanoacetate (IV) and dimethyl sulfate for the addition mentioned above is preferably almost 1:2 (1:2.0–2.5). The temperature of the above-mentioned addition is preferably 20–60° C., more preferably 35–45° C. When the above-mentioned temperature is lower than 20° C., the reaction becomes late and may proceed beyond control due to sudden heat generation caused by the reaction. When the above-mentioned temperature exceeds 60° C., the yield may become lower due to the side reaction.

By adding cyanoacetate (IV) and dimethyl sulfate to an NaH-containing THF solution as mentioned above at the aforementioned molar ratio and temperature, generation of hydrogen and heat due to the reaction can be controlled by the rate of addition of cyanoacetate (IV) and dimethyl sulfate. The reaction mixture under such conditions becomes a slurry having a relatively lower viscosity, where sodium monomethylsulfate has precipitated out.

In the above-mentioned production method, both dropwise addition or in-flowing may be employed. The time necessary for the addition is free of any particular limitation as long as the reaction heat can be removed, the amount of hydrogen generated is below excess and the temperature stays within the range to be mentioned below, and varies depending on the scale of the reaction.

In the production method of the above-mentioned 2-cyano-2,2-dimethylacetate (II), a part of either cyanoacetate (IV) or dimethyl sulfate may be charged in advance in an NaH-containing THF solution. In this case, cyanoacetate (IV) is preferably charged in advance in a preferable proportion of 5 wt %–20 wt %, more preferably 5 wt %–10 wt %, of the entire amount to be used for the reaction.

After the reaction shown in the above-mentioned Scheme 2, the reaction mixture is treated with, for example, a dilute aqueous acetic acid solution, a THF layer is extracted, THF is evaporated at the atmospheric pressure—under somewhat reduced pressure (20–26.6 kPa), and then evaporated under reduced pressure of 1.3–1.6 kPa, whereby 2-cyano-2,2-dimethylacetate (II) can be obtained at 62–69° C.

By the production method shown in the above-mentioned Scheme 2, 2-cyano-2,2-dimethylacetate (II) can be produced in a yield of not less than 80%, particularly not less than 85%.

The β-keto ester compound (I) of the present invention is preferably obtained economically in a high yield by obtaining 2-cyano-2,2-dimethylacetate (II) from the reaction of cyanoacetate (IV) with dimethyl sulfate according to the method shown in the aforementioned Scheme 2, and then reacting 2-cyano-2,2-dimethylacetate (II) with an alkyl ester (III) according to the method shown in the aforementioned Scheme 1. As mentioned above, it is particularly preferable that $R_1$ be methyl group or ethyl group and the method of Scheme 1 be realized by dropwise addition of a lithium diisopropylamide solution to a mixture of ethyl 2,2-dimethylcyanoacetate and tert-butyl acetate.

β-Hydroxy Acid Compound (V) and Production Method Thereof

In the present invention, a production method of a novel β-hydroxy acid compound (V) of the following formula

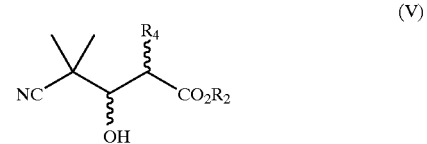

(V)

wherein $R_2$ and $R_4$ are as mentioned above, provided that when $R_4$ is alkyl group having 1 to 6 carbon atoms, $R_2$ should be tert-butyl group, is also provided, which comprises reducing a β-keto ester compound of the following formula

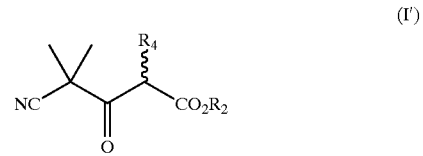

(I')

wherein $R_2$ and $R_4$ are as mentioned above, provided that when $R_4$ is alkyl group having 1 to 6 carbon atoms, $R_2$ should be tert-butyl group (hereinafter sometimes to be referred to as β-keto ester compound (I')) or a salt thereof.

The production method of β-hydroxy acid compound (V) of the present invention comprises adding a reducing agent to β-keto ester compound (I') to allow reaction.

The reducing agent to be used for the reduction may be any as long as it can reduce β-keto ester compound (I') to β-hydroxy acid compound (V) (one capable of reducing oxo(ketone) group to hydroxy group), which is exemplified by alkali borohydride such as sodium borohydride, lithium borohydride and the like, diisobutylaluminum hydride and the like. Of these, alkali borohydride, particularly sodium borohydride, is preferable because the objective compound can be obtained quantitatively.

The amount of the reducing agent to be added is free of any particular limitation, but is preferably 0.25–1.0 mol, more preferably 0.3–0.7 mol, per 1 mol of the β-keto ester compound (I'). When the amount of the reducing agent to be added is less than 0.25 mol per 1 mol of the β-keto ester compound (I'), the reaction cannot be completed and the yield tends to be lower. When the amount of the reducing agent to be added exceeds 1.0 mol per 1 mol of the β-keto ester compound (I'), it may lead to an economical burden.

In this reduction reaction, the reaction temperature varies depending on the starting materials. When, for example, a β-keto ester compound of the following formula

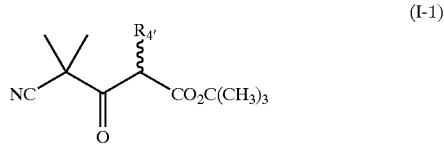

(I-1)

wherein $R_{4'}$ is as defined above, which is a compound of the above-mentioned formula (I') wherein $R_4$ is alkyl group ($R_{4'}$) having 1 to 6 carbon atoms and $R_2$ is tert-butyl group, is used as a starting material, it is preferably from 0° C. to 30° C., because the reaction speed and stereoselectivity can be maintained high. When the reaction temperature is lower than 0° C., the reaction speed may become slow and the reaction time may be prolonged. When the reaction temperature exceeds 30° C., stereoselectivity may become lower. The reaction time in this case is preferably 0.25–10 hr. Moreover, when a β-keto ester compound of the following formula

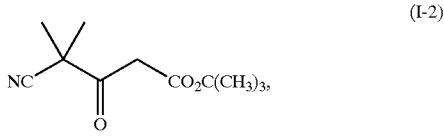

(I-2)

which is a compound of the above-mentioned formula (I') wherein $R_4$ is hydrogen atom and $R_2$ is tert-butyl group, is used as a starting material, the reaction temperature is generally 0–50° C., preferably 10–30° C., and the reaction time may be any as long as the reaction heat can be controlled, which is preferably 2–10 hr.

The solvent to be used for the above-mentioned reduction may be any as long as it is inert to the above-mentioned reducing agent and can be selected as appropriate depending on the reducing agent to be used. For example, when sodium borohydride is used as a reducing agent, the usable solvent includes water, alcohol solvents (e.g., methanol, ethanol, 2-propanol), ester solvents, ether solvents (e.g., tetrahydrofuran (THF), dioxane), and mixed solvents thereof. Of these, alcohol solvents are preferable because stereoselectivity and reaction speed can be high and by-product is produced only in a smaller amount. In addition, when diisobutylaluminum hydride, which requires an aprotic solvent, is used as a reducing agent, ether solvents (e.g., THF, ether), hydrocarbon solvents (e.g., toluene, hexane, cyclohexane) and the like can be used, of which dry THF is preferably used.

While the amount of the above-mentioned solvent to be used is free of any particular limitation, it is preferably from a 0.5-fold amount to a 10-fold amount, more preferably from a 1-fold weight to a 2-fold weight, relative to the weight of the β-keto ester compound (I'). When the amount of the above-mentioned solvent to be used is less than 0.5-fold amount relative to the β-keto ester compound (I'), stirring does not proceed smoothly and uniform progress of the reaction may be prevented. When the amount of the above-mentioned solvent to be used exceeds a 10-fold amount relative to the β-keto ester compound (I'), the volume efficiency may become low, which is uneconomical.

It is also possible to reduce β-keto ester compound (I') into β-hydroxy acid compound (V) by catalytic reduction.

The β-keto ester compound (I') to be used for this reaction can be produced by a method the same as or similar to the production method of the aforementioned β-keto ester compound (I).

In this way, β-hydroxy acid compound (V) of the following formula (V)

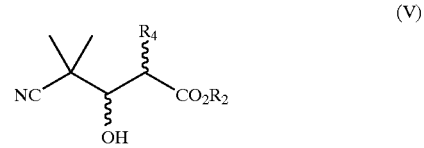

(V)

wherein $R_2$ and $R_4$ are as defined above, provided that when $R_4$ is alkyl group ($R_{4'}$) having 1 to 6 carbon atoms, $R_2$ should be tert-butyl group, can be produced.

A compound of the following formula

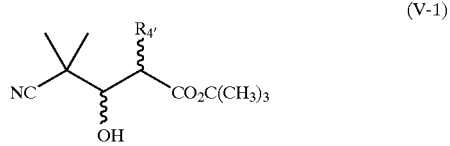

(V-1)

wherein $R_{4'}$ is alkyl group having 1 to 6 carbon atoms, which is the above-mentioned β-hydroxy acid compound (V) wherein $R_4$ is alkyl group having 1 to 6 carbon atoms and $R_2$ is tert-butyl group, encompasses the following four optical isomers

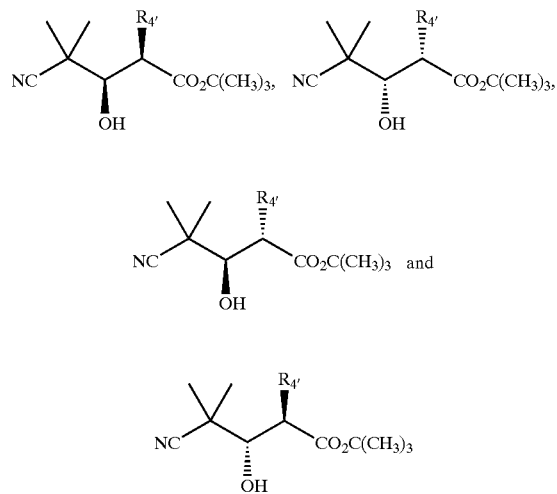

wherein $R_4$ is as defined above.

A compound of the following formula (V-2)

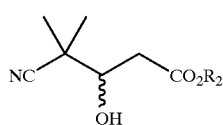
(V-2)

wherein $R_1$ is as defined above, which is a β-hydroxy acid compound (V) wherein $R_4$ is hydrogen atom, encompasses the following two optical isomers

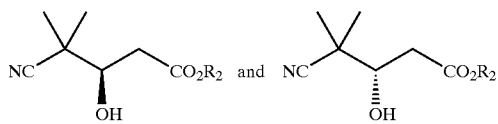

wherein $R_2$ is as defined above.

The β-hydroxy acid compound (V) of the present invention encompasses an optically active form, mixtures thereof (racemate, enantiomer mixture, diastereomer mixture) and the like. Furthermore, β-hydroxy acid compound of the following formula (V-3)

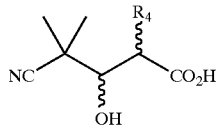
(V-3)

wherein $R_4$ is as defined above, which is the above-mentioned β-hydroxy acid compound (V) wherein $R_2$ is hydrogen atom, can form a salt. The β-hydroxy acid compound (V) of the present invention also encompasses a salt form. Examples of the salt include alkali metal salts such as sodium, potassium etc., organic amine salts such as triethylamine salt etc., and the like.

This β-hydroxy acid compound (V) is also a novel compound found for the first time by the present inventors and extremely useful as a synthetic intermediate for the production of an epothilone derivative under development as a pharmaceutical agent having antitumor activity.

The aforementioned production method is merely an example of the method for producing β-hydroxy acid compound (V), and β-hydroxy acid compound (V) of the present invention is not limited to those produced by the above-mentioned production method. However, it is preferably produced by the above-mentioned production method.

The present inventors have further found that, when alkali borohydride is used as a reducing agent in the production method of the above-mentioned β-hydroxy acid compound (V), the ratio of stereo isomers of the resulting β-hydroxy acid compound (V) can be changed by the presence or otherwise of a divalent metal salt during the reduction reaction.

That is, taking the above-mentioned β-hydroxy acid compound of the following formula

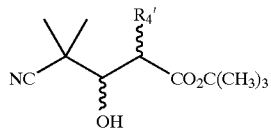
(V-1)

wherein $R_{4'}$ is alkyl group having 1 to 6 carbon atoms, which is a compound of the above-mentioned formula (V) wherein 4 is alkyl group ($R_{4'}$) having 1 to 6 carbon atoms and $R_2$ is tert-butyl group, (hereinafter sometimes to be referred to as β-hydroxy acid compound (V-1)) as an example, a threo form isomers

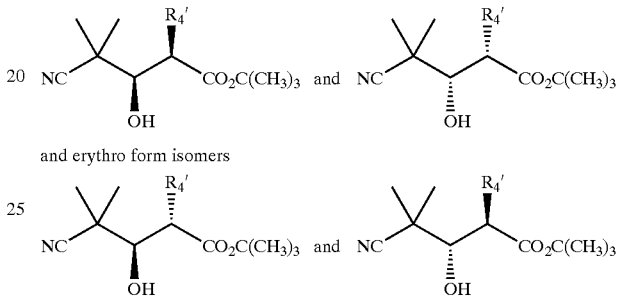

and erythro form isomers are produced according to the production method of the above-mentioned β-hydroxy acid compound (V). According to the present invention, the ratio of the resulting threo form and erythro form changes depending on the presence/absence of a divalent metal chloride during the above-mentioned reaction.

Specifically, when a divalent metal chloride is absent during the above-mentioned reduction, the ratio of the resulting threo form and erythro form is threo form:erythro form=91.9:8.1–90:10, and when the above-mentioned metal chloride is present, the ratio of the resulting threo form and erythro form is threo form:erythro form=68.8:31.2–46.7:53.3.

As the divalent metal chloride to be used in the present invention, for example, manganese(II) chloride ($MnCl_2$), calcium chloride ($CaCl_2$), zinc(II) chloride ($ZnCl_2$) and the like are exemplified, wherein the use of manganese(II) chloride or calcium chloride is preferable, in view of the low reactivity of zinc(II) chloride.

When the above-mentioned metal chloride is used, the amount thereof to be added is free of any limitation and can be determined appropriately according to the reactivity of the β-keto ester compound (I'). Because β-keto ester compound (I') is highly likely bonded coordinately with the metal chloride at a ratio of 1:1, the amount is preferably 1–3 mol, more preferably 1.5–2 mol, relative to 1 mol of the β-keto ester compound (I'). When the amount of the above-mentioned metal chloride to be added is less than 1 mol relative to 1 mol of the β-keto ester compound (I'), the ideal stereoselectivity is highly likely not achieved. When the amount of the metal chloride to be added exceeds 3 mol relative to 1 mol of the β-keto ester compound (I'), an economical burden may increase.

The β-hydroxy acid compound (V) can be isolated and purified by subjecting the reaction mixture after the above-mentioned reduction to typical treatment and separation. For example, an organic solvent is added to the reaction mixture and the mixture is stirred and partitioned to remove the organic layer, the pH of the aqueous layer is adjusted, the aqueous layer is subjected to extraction with a solvent and the extract is concentrated to isolate the above-mentioned hydroxy acid compound (V).

The organic solvent to be added to the reaction mixture after reduction is exemplified by heptane, toluene, ethyl acetate, MIBK (methyl isobutyl ketone) and the like, with preference given to toluene in view of the low affinity for water and easy extraction. The time for stirring upon addition of the organic solvent is not particularly limited as long as the organic layer and the aqueous layer are sufficiently separated. The pH of the aqueous layer is adjusted to an acidic one (generally 1–3, preferably 1.5–2.5) using an acid such as hydrochloric acid, sulfuric acid and the like.

The above-mentioned solvent used for extraction of the objective β-hydroxy acid compound (V) from the aqueous layer is free of any particular limitation and is exemplified by ethyl acetate, a mixed solution of ethyl acetate-n-butanol (1:1), toluene and the like, with preference given to toluene that resists mixing of water. Removal of the solvent (the above-mentioned alcohol solvent and the like) under reduced pressure before extraction facilitates, extraction with toluene.

The a β-hydroxy acid compound (V-2) of the following formula

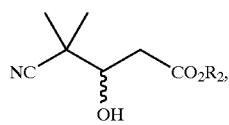

(V-2)

which is a β-hydroxy acid compound (V) wherein $R_4$ is hydrogen atom, is exemplified by (1) the above-mentioned β-hydroxy acid compound of the following formula

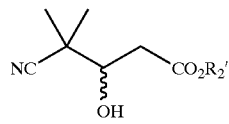

(V-4)

wherein $R_{2'}$ is alkyl group having 1 to 6 carbon atoms, (hereinafter sometimes to be referred to as β-hydroxy acid compound (V-4)), which is a β-hydroxy acid compound (V) wherein $R_2$ is alkyl group ($R_{2'}$) having 1 to 6 carbon atoms and $R_4$ is hydrogen atom, (2) β-hydroxy acid compound of the following formula

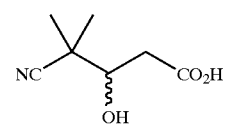

(V-5)

(hereinafter sometimes to be referred to as β-hydroxy acid compound (V-5)), which is a β-hydroxy acid compound (V) wherein $R_2$ and $R_4$ are both hydrogen atoms, (3) β-hydroxy acid compound of the following formula

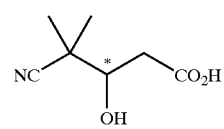

(V-6)

(hereinafter sometimes to be referred to as β-hydroxy acid compound (V-6)), which is an optically active form of the above-mentioned β-hydroxy acid compound (V-5), and (4) β-hydroxy acid compound of the following formula

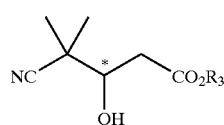

(V-7)

wherein $R_3$ is alkyl group having 1 to 6 carbon atoms, (hereinafter sometimes to be referred to as β-hydroxy acid compound (V-7)), which is an ester of the above-mentioned β-hydroxy acid compound (V-6).

The β-hydroxy acid compounds (V-5) to (V-7) can be produced by the aforementioned production method of the β-hydroxy acid compound (V), and also by the following method.

Production Method of β-hydroxy Acid Compound (V-5) Using β-hydroxy Acid Compound (V-4) as a Starting Material The β-hydroxy acid compound (V-5) (4-cyano-3-hydroxy-4-methylpentanoic acid) is also a novel compound, and can be obtained by alkali hydrolysis of β-hydroxy acid compound (V-4) as shown in the following Scheme 4.

[Scheme 4]

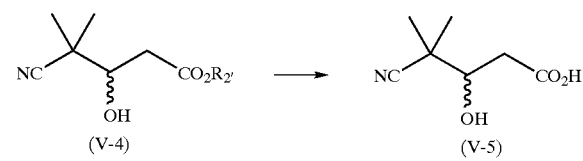

In the above-mentioned Scheme 4, $R_{3'}$ is as defined above.

The β-hydroxy acid compound (V-4) can be produced according to the production method of the aforementioned β-hydroxy acid compound (V) (hereinafter sometimes to be referred to as Step 1). Therefore, alkali hydrolysis of β-hydroxy acid compound (V-4) (hereinafter sometimes to be referred to as Step 2) is preferably performed successively from the production method of the β-hydroxy acid compound (V) to reduce the number of steps. To be specific, β-hydroxy acid compound (V-5) can be obtained without isolation of β-hydroxy acid compound (V-4), by dropwise addition of an alkali solution to a solution containing a reducing agent in the above-mentioned step 1. Alternatively, water is added to a solution containing a reducing agent in the above-mentioned step 1, to separate the inorganic compound resulting from the reducing agent, which compound is subjected to alkali hydrolysis to give β-hydroxy acid compound (V-5).

The above-mentioned alkali solution may be any as long as it can hydrolyze an alkyl group of the ester to give carboxyl group. Examples thereof include aqueous sodium hydroxide solution, aqueous potassium hydroxide solution, aqueous sodium carbonate solution, aqueous potassium carbonate solution and the like. Of these, 10% aqueous sodium hydroxide solution is preferable, in consideration of the hydrolysis speed and foaming during neutralization. The amount of the alkali solution to be added is generally 1–4 equivalent amount, preferably 1.5–3 equivalent amount, relative to hydroxy acid compound (V-4), on conversion to β-hydroxy acid alkali salt compound.

Simultaneously with or before addition of the alkali solution, a solvent such as methanol and the like is preferably added to β-hydroxy acid compound (V-4) for efficient progress of hydrolysis. The amount of the solvent to be added is, for example, generally 0.05-fold volume to 2-fold volume, preferably 0.1-fold volume to 1-fold volume, of the solvent in the solution containing a reducing agent in the above-mentioned Step 1.

The time of hydrolysis is up to the disappearance of β-hydroxy acid compound (V-4), which is generally 1–10 hr, preferably 2–5 hr, and the temperature is generally 0–60° C., preferably 10–40° C.

The reaction mixture after hydrolysis is isolated and purified by a typical step for treatment and separation. For example, an organic solvent is added to the reaction mixture and the mixture is stirred and partitioned to remove the organic layer, the pH of the aqueous layer is adjusted, the aqueous layer is subjected to extraction with a solvent and concentrated to isolate β-hydroxy acid compound (V-5). The organic solvent to be added after hydrolysis is exemplified by heptane, toluene and the like, preferably toluene. The time for stirring upon addition of the organic solvent is not particularly limited as long as the organic layer and the aqueous layer are thoroughly separated. The pH of the aqueous layer is adjusted to an acidic one (generally 0–3, preferably 1–2) with an acid such as hydrochloric acid, sulfuric acid and the like. The solvent used for extraction of the objective β-hydroxy acid compound (V-5) from the aqueous layer is exemplified by ethyl acetate, a mixture of ethyl acetate-n-butanol (1:1) and the like. The use of ethyl acetate as a solvent is preferable, because the yield becomes high and the objective β-hydroxy acid compound (V-5) can be obtained as crystals. The β-hydroxy acid compound (V-5) obtained as crystals has a comparatively high purity, which is preferable for forming a salt with optically active amine in the next optical resolution step. In addition, extraction is preferably carried out twice.

Production Method of β-hydroxy Acid Compound (V-6) by Optical Resolution of β-hydroxy Acid Compound (V-5)

As shown in the following Scheme 5, β-hydroxy acid compound (V-5) is optically resolved (hereinafter sometimes to be referred to as Step 3) to give S-form or R-form of β-hydroxy acid compound (V-6). For example, by optical resolution by the diastereomeric isomer crystallization method for forming a salt of β-hydroxy acid compound (V-5) with S-form or R-form of the optically active compound, S-form or R-form of β-hydroxy acid compound (V-6) can be obtained.

[Scheme 5]

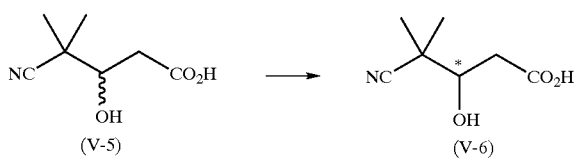

Specifically, as an optically active compound reagent for optical resolution, optically active amine is used to give crystals of diastereomer salt, which salt is decomposed (i.e., liberation of amine) to give β-hydroxy acid compound (V-6). The β-hydroxy acid compound (V-5) to be the starting material in this Step 3 can be produced by, for example, the above-mentioned Step 1 or 2.

The optically active compound to be used for this reaction may be any as long as it forms a salt with β-hydroxy acid compound (V-5) and permits optical resolution of β-hydroxy acid compound (V-6) at a high optical purity. Examples thereof include optically active amine compound. Particularly, R-(+)-N-(p-hydroxybenzyl)phenylethylamine of the following formula

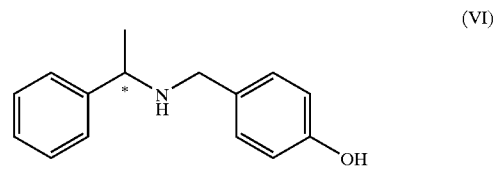

(VI)

(R-HBPEA; hereinafter sometimes to be referred to as optically active amine compound (VI)) is preferable, because optical resolution is performed and the aimed optical compound is obtained at a high optical purity in a high yield. The optically active amine compound (VI) in the R-form can be obtained according to the production method disclosed in JP patent No. 3031048. The production example therein is shown in Reference Example below. In the following, Step 3 is explained by referring to an example using an optically active amine compound (VI) as an optically active compound. However, Step 3 is not limited to this example.

To be specific, β-hydroxy acid compound (V-5) is dissolved in the following solvent. The above-mentioned optically active amine compound (VI) is added to this solution, and the mixture is stirred while raising the temperature until the precipitated salt is dissolved, after which the mixture is cooled until the salt is precipitated and stirred. The mixture is gradually cooled and, after stirring further at a given temperature, filtrated, washed with a solvent and dried to give an amine salt of β-hydroxy acid compound (V-6) having a high optical purity.

The solvent in which to dissolve β-hydroxy acid compound (V-5) is exemplified by water; alcohol solvents represented by methanol, ethanol and 2-propanol; ester solvents represented by ethyl acetate; and mixed solvents thereof; and the like. of these, ethyl acetate, methanol, water, and mixed solvents thereof are preferable from the aspect of efficiency of the optical resolution. The amount of the solvent to be used is generally 5–25 L, preferably 7–20 L, relative to 1 kg of hydroxy acid compound (V-5).

The amount of the optically active amine compound (VI) to be used is generally 0.4–1.1 mol, preferably 0.5–1.0 mol, per 1 mol of β-hydroxy acid compound (V-5).

After the addition of optically active amine compound (VI), the temperature of the mixture is generally raised to the boiling point of the solvent or mixture for dissolution of the precipitated salt. When dissolution of the salt is insufficient, the solvent is added until the salt is dissolved. Examples of the solvent include methanol, water, ethyl acetate and the like, preferably methanol and water. The amount of the solvent to be used is generally 0.1–7 L, preferably 1–4 L, per 1 kg of β-hydroxy acid compound (V-5).

For gradual cooling and stirring until the salt is sufficiently precipitated, the temperature of precipitation is generally from the boiling point of the solvent to 0° C., preferably 65–10° C., and the stirring time is generally 2–12 hr.

The solvent to be used for washing after filtration is preferably a solvent having the composition of the solvent used for precipitation. The amount of the solvent to be used for washing is not particularly limited and is an amount sufficient to thoroughly wash the filtrated product.

Besides the above-mentioned procedure of obtaining optically resolved amine salt, the following procedure can be adopted, i.e., the addition of optically active amine to the solution, temperature raising, stirring and cooling of the solution to obtain optically resolved amine salt, it is possible to gradually allow precipitation of the salt by adding a solution of optically active amine compound (VI) to a solution of β-hydroxy acid compound (V-5) at a temperature of from room temperature to around 40° C., and then to allow cooling. For precipitation of the salt, a poorly dissolving solvent (toluene and the like) may be added to a solution containing an acid (β-hydroxy acid compound (V-5)) and amine to allow precipitation of crystals.

Optical Resolution (Recrystallization) of β-hydroxy Acid Compound (V-6)

Recrystallization gives an amine salt of β-hydroxy acid compound (V-6) having a higher optical purity than that of an amine salt of β-hydroxy acid compound (V-6) obtained in the above-mentioned Step 3. To be specific, a salt of the β-hydroxy acid compound (V-6) obtained by the above-mentioned Step 3 is mixed with a solvent to dissolve the salt, and the mixture is gradually cooled. Seed crystals are added at a suitable temperature and the mixture is then gradually cooled and, after further stirring at a given temperature, filtrated, washed with a solvent and dried to increase the optical purity than the amine salt of β-hydroxy acid compound (V-6) obtained in the above-mentioned Step 3.

For recrystallization, a solvent to dissolve a salt of β-hydroxy acid compound (V-6) may be the same as the solvent in which β-hydroxy acid compound (V-6) is dissolved in the above-mentioned Step 3, and preferable solvents are the same. The amount of these solvents to be used for recrystallization is generally 5–20 L, preferably 6–15 L, per 1 kg of a salt of β-hydroxy acid compound (V-6).

The temperature of the solution of a salt of β-hydroxy acid compound (V-6) mixed with these solvents is generally raised to the boiling point of the solvent or mixture, and a different solvent is added until the salt is dissolved. As this solvent, methanol, water and the like are preferable. The amount of the solvent to be used is generally 0.1–5 L per 1 kg of a salt of β-hydroxy acid compound (V-6).

The solution is gradually cooled and stirred after adding seed crystals at a suitable temperature. The stirring time is generally 15 min–3 hr. The reaction mixture is gradually cooled generally to room temperature (35° C.)-0° C., preferably 20–10° C., over 30 min to 12 hr.

The solvent to be used for washing after filtration is desirably a solvent having the composition for crystal precipitation.

The obtained amine salt of β-hydroxy acid compound (V-6) is converted to a β-hydroxy acid compound (V-6) by releasing the amine. The β-hydroxy acid compound (V-6) can be used as a starting material for the next esterification step. The amine salt of β-hydroxy acid compound (V-6) can be decomposed into a β-hydroxy acid compound (V-6) and an optically active amine compound (VI) (R-HBPEA) by a conventional method. For example, the amine salt of β-hydroxy acid compound (V-6) is added to water, a base in an equivalent or more amount and a solvent are added and a partitioned organic layer is removed to separate the amine.

Production Method of β-hydroxy Acid Compound (V-7) Using β-hydroxy Acid Compound (V-6) as a Starting Material The β-hydroxy acid compound (V-7) is also a novel compound, and can be obtained by esterification of β-hydroxy acid compound (V-6) or a salt thereof with an alkylating agent as shown in, for example, the following Scheme 6. The salt of β-hydroxy acid compound (V-6) is exemplified by those mentioned with regard to the salt of β-hydroxy acid compound (V).

[Scheme 6]

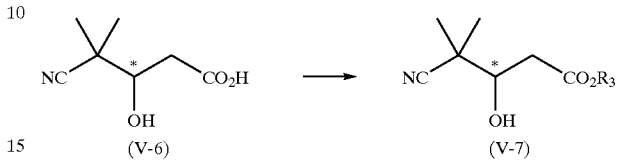

In the above-mentioned Scheme, $R_3$ is as defined above.

Specifically, the esterification of β-hydroxy acid compound (V-6) or a salt thereof with an alkylating agent (hereinafter sometimes to be referred to as Step 4) varies depending on the use of a free form of β-hydroxy acid compound (V-6) (Method 1) and a salt (e.g., amine salt) of β-hydroxy acid compound (V-6) (Method 2) as a starting material. The hydroxy acid compound (V-6) to be used as a starting material in this Step 4 can be produced by, for example, the above-mentioned Step 1 or Step 3.

Method 1: A free form of β-hydroxy acid compound (V-6) is dissolved in a solvent and an alkylating agent is added for esterification in the presence of a base.

Method 2: A salt of β-hydroxy acid compound (V-6) (e.g., amine salt) and a solvent for extraction are added to water. To the mixture, an equivalent or more amount of a base is added, and the organic layer containing the amine is separated and removed. A solvent is added to an aqueous layer containing β-hydroxy acid compound (V-6), and, for example, an alkylating agent is added for esterification in the presence of a phase transfer catalyst.

In Method 1 and Method 2, the same alkylating agent may be used. The alkylating agent is free of any particular limitation and can be appropriately determined according to the objective β-hydroxy acid compound (V-7). Examples thereof include dimethyl sulfate, diethyl sulfate, methyl bromide, ethyl bromide, allyl bromide, benzyl chloride, benzyl bromide and the like. of these, dimethyl sulfate is preferably used in view of reactivity.

In Method 1, the solvent to dissolve β-hydroxy acid compound (V-6) is exemplified by N,N-dimethylformamide (DMF), dimethyl sulfoxide (DMSO), N,N-dimethyl acetamide, acetonitrile and the like, with preference given to DMF in view of the economic aspect and reactivity. The amount of the solvent to be used is generally 2–15 L, preferably 5–10 L, per 1 kg of β-hydroxy acid compound (V-6).

The base to be used along with the alkylating agent in Method 1 is exemplified by potassium carbonate, N,N-diisopropylethylamine, triethylamine, sodium carbonate and the like. Of these, potassium carbonate and sodium carbonate are preferable from the aspect of reactivity. The amount of the base to be used is generally 1–5 equivalent amount, preferably 1–4 equivalent amount relative to β-hydroxy acid compound (V-6), and the amount of the alkylating agent to be used is generally 1–3 mol, preferably 1–2 mol, relative to 1 mol of β-hydroxy acid compound (V-6). The reaction time necessary for the esterification is generally 0.5–8 hr, preferably 1–5 hr.

In Method 2, an amine salt of β-hydroxy acid compound (V-6) is added to water, and a base such as sodium hydroxide, sodium carbonate, potassium hydroxide and the like, a solvent (e.g., toluene, ethyl acetate, preferably toluene) for extracting amine, and the like are added.

The solvent to be added to the aqueous layer containing β-hydroxy acid compound (V-6) in Method 2 is free of any particular limitation as long as it is an organic solvent suitable for extracting β-hydroxy acid compound (V-7) produced by esterification. Examples thereof include toluene, ethyl acetate and the like, preferably toluene.

The phase transfer catalyst to be added for alkylation in Method 2 is exemplified by tetrabutylammonium bromide, benzyltriethylammonium chloride and the like. Of these, tetrabutylammonium bromide is preferable from the economical aspect.

In Method 2, the amount of the alkylating agent to be used is generally 1–3 mol, preferably 1–2 mol relative to 1 mol of a salt (amine salt) of β-hydroxy acid compound (V-6), and the amount of the base to be used is generally 1–4 equivalent amount, preferably 1–3 equivalent amount, relative to a salt (amine salt) of β-hydroxy acid compound (V-6). The reaction time necessary for esterification is generally 0.5–8 hr, preferably 1–5 hr.

In Method 1 and Method 2, β-hydroxy acid compound (V-7) can be isolated and purified from the reaction mixture after the above-mentioned esterification by general post-treatment and separation. In the case of Method 1, for example, an organic solvent is added to the reaction mixture after esterification, pH is adjusted, the solution is partitioned, an organic layer is extracted, an aqueous layer is extracted again with an organic solvent, and the combined organic layers are concentrated under reduced pressure to isolate and purify β-hydroxy acid compound (V-7). In the case of Method 2, for example, an organic layer of the reaction mixture after esterification is extracted, where necessary, an aqueous layer is extracted again, and the combined organic layers are concentrated under reduced pressure to isolate and purify β-hydroxy acid compound (V-7).

Acetonide Form and Optically Active Form of 1.3-diol Derivative and Production Methods Thereof The present invention further provides a production method of the above-mentioned acetonide form (VIII) or an optically active form thereof of the following formula (VIII) (hereinafter sometimes to be referred to as acetonide form (VIII)), which comprises converting a 1,3-diol derivative of the following formula (VII) or an optically active form thereof (hereinafter sometimes to be referred to as 1,3-diol derivative (VII)) to acetonide as shown in the following Scheme 7.

[Scheme 7]

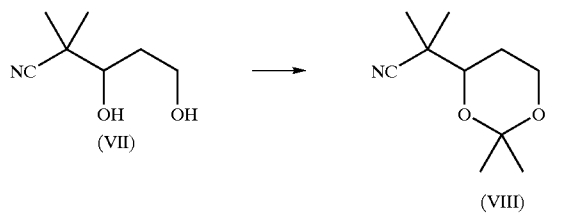

The reaction to give acetonide form (VIII) from 1,3-diol derivative (VII) comprises, for example, (A) adding a catalytic amount of an acid catalyst to a solution of 1,3-diol derivative (VII) in 2,2-dimethoxypropane or 2-methoxypropene, (B) adding a catalytic amount of an acid catalyst to a solution of 1,3-diol derivative (VII) in acetone in the presence of a dehydrating agent, or (C) reacting 1,3-diol derivative (VII) with orthoformate and acetone. The respective solvents in the above-mentioned (A)–(C) may be the reaction reagents themselves and may be used in an amount of generally 3–20 parts by weight, preferably 3.5–10 parts by weight, per 1 part by weight of 1,3-diol derivative (VII).

The acid catalyst to be used for the above-mentioned (A) and (B) is not particularly limited and exemplified by p-toluenesulfonic acid, pyridine p-toluenesulfonic acid salt, camphorsulfonic acid and the like. The acid catalyst is used in an amount of generally 0.5–15 parts by weight, preferably 2–15 parts by weight, per 100 parts by weight of 1,3-diol derivative (VII).

The above-mentioned (A)–(C) are carried out at a temperature of generally from 0° C. to the boiling point of the solvent.

The dehydrating agent to be used for the above-mentioned (B) is exemplified by anhydrous copper sulfate.

The orthoformate to be used for the above-mentioned (C) is exemplified by methyl orthoformate and ethyl orthoformate and is used in an amount of generally 3–20 parts by weight, preferably 3.5–10 parts by weight, per 1 part by weight of 1,3-diol derivative (VII).

The 1,3-diol derivative (VII), which is a starting material, can be obtained from the above-mentioned β-hydroxy acid compound (V-2) of the following formula

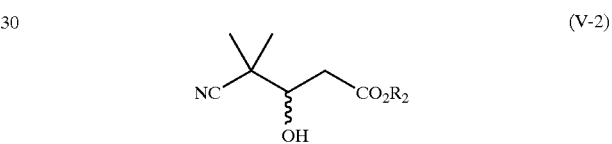

wherein $R_2$ is as defined above.

That is, as shown in the following Scheme 8, acetonide form (VIII) can be produced using β-hydroxy acid compound (V-2) as a starting substance via 1,3-diol derivative (VII).

[Scheme 8]

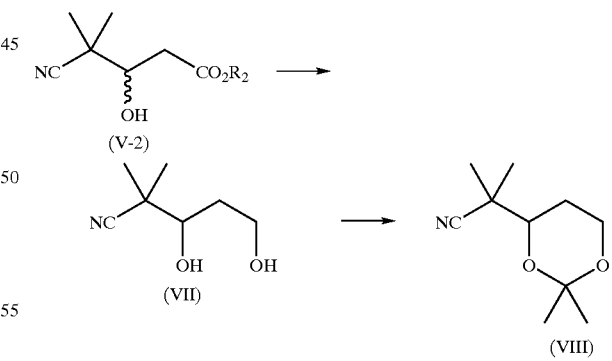

In the above-mentioned Scheme, $R_2$ is as defined above.

In the production method of acetonide form (VIII), β-hydroxy acid compound (V-2), which is the starting substance, can be produced, for example, according to the method the same as or similar to the above-mentioned "β-keto ester compound (I) and production method thereof" and "β-hydroxy acid compound (V) and production method thereof", through β-keto ester compound of the following formula

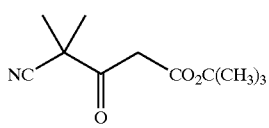

which is β-keto ester compound (I) wherein $R_4$ is hydrogen atom, as shown in following Scheme 9.

[Scheme 9]

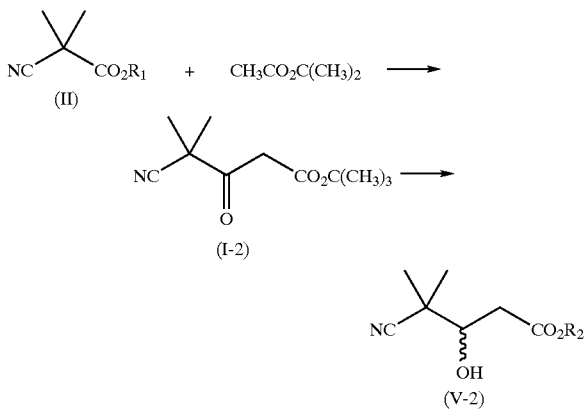

In the above-mentioned Scheme, $R_1$ and $R_2$ are as defined above.

The reduction of β-hydroxy acid compound (V-5) or β-hydroxy acid compound (V-6) to 1,3-diol derivative (VII) is carried out generally using 2 to 8 molar amount of a reducing agent per 1 mol of p-hydroxy acid compound (V-5) or β-hydroxy acid compound (V-6). Examples of the reducing agent include borane, borane complex such as borane-THF complex and the like. Of these, a borane complex (e.g., borane-THF complex) is preferable in view of availability and handling property. As the reaction solvent, ethers such as tetrahydrofuran (THF), 1,2-dimethoxyethane and the like, hydrocarbons such as toluene and the like and mixed solvents thereof are used. The reaction solvent is generally used in an amount of 2- to 10-fold volume amount (2–10 ml) per 1 part by weight (1 g) of β-hydroxy acid compound (V-5) or β-hydroxy acid compound (V-6). The reaction temperature is generally −10° C. to 30° C., preferably 0° C., and the reaction time is generally 1–6 hr, preferably 3 hr.

To be specific, for example, a borane-THF complex is added to a solution of β-hydroxy acid compound (V-5) or β-hydroxy acid compound (V-6) in THF at −10° C. to 30° C. (preferably 0° C.) and the mixture is reacted for 1–6 hr (preferably 3 hr).

The reduction of β-hydroxy acid compound (V-4) or β-hydroxy acid compound (V-7) to 1,3-diol derivative (VII) is carried out using metal hydride generally in an amount of 0.5–5 mol (preferably 1–3 mol) per 1 mol of p-hydroxy acid compound (V-4) or β-hydroxy acid compound (V-7). The above-mentioned metal hydride is exemplified by hydrides of boron and aluminum, such as sodium borohydride, lithium borohydride, diisobutylaluminum hydride and diborane. Of these, sodium borohydride is preferably used from the economical aspect. The reduction is carried out in ethers such as THF and the like, lower alcohols having 1 to 4 carbon atoms such as methanol, ethanol and the like, water and a mixed solvent thereof. The amount of the solvent to be used is generally 5- to 20-fold volume (5–20 ml) amount per 1 part by weight (1 g) of β-hydroxy acid compound (V-4) or β-hydroxy acid compound (V-7). The reduction is generally carried out at a temperature of around 0° C. to about 40° C., preferably 10–30° C. For example, 0.5–3 equivalents (preferably 2 equivalents) of sodium borohydride are added to a mixed solution of β-hydroxy acid compound (V-4) or β-hydroxy acid compound (V-7) in THF-methanol at 0–40° C. (preferably around room temperature) and the mixture is reacted for 0.15–5 hr (preferably 3 hr). The completion of the reduction is when the peak of the starting material disappears by detection using gas chromatography and the like.

When a racemate of β-hydroxy acid compound (V-4) or hydroxy acid compound (V-5) is used as a starting substance for the synthesis of acetonide form (VIII) through the above-mentioned 1,3-diol derivative (VII), a reagent for optical resolution as used in the above-mentioned Step 3 is used at some stage in the aforementioned reaction, thereby to obtain an optically active acetonide form alone from the racemic intermediate. This optical resolution may be conducted at any stage, but β-hydroxy acid compound (V-6) or β-hydroxy acid compound (V-7), which is an optically active form, is preferably used as a starting substance in view of operability of the optical resolution. Preferably, β-hydroxy acid compound (V-6) or β-hydroxy acid compound (V-7) is subjected to the synthesis of 1,3-diol derivative (IX), as mentioned earlier, to give an optically active 1,3-diol derivative of the following formula

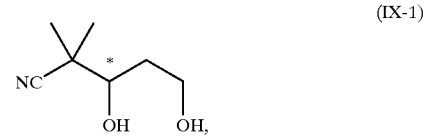

and this optically active 1,3-diol derivative is converted to an optically active acetonide form of the following formula

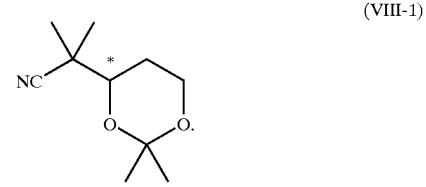

The acetonide forms (VIII) and (VIII-1) of the present invention can be used as a constituent factor of the portion enclosed with a broken line in the following formulas showing the epothilone derivatives according to various conventionally known methods.

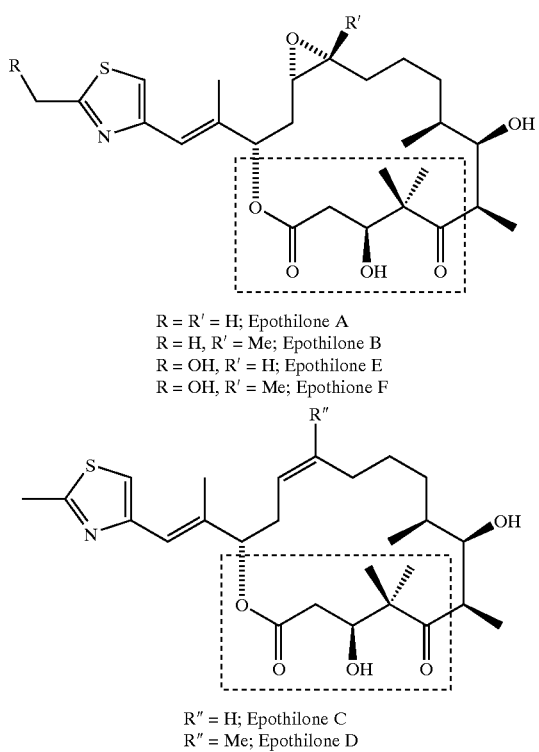

R = R' = H; Epothilone A
R = H, R' = Me; Epothilone B
R = OH, R' = H; Epothilone E
R = OH, R' = Me; Epothione F R" = H; Epothilone C
R" = Me; Epothilone D Using β-hydroxy acid compound (V-1) of the following formula

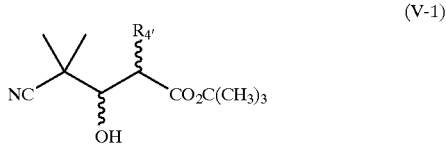

(V-1)

wherein $R_{4'}$ is alkyl group having 1 to 6 carbon atoms, or an optically active form thereof, which is a compound of the formula (V) wherein $R_4$ is alkyl group ($R_{4'}$) having 1 to 6 carbon atoms and $R_2$ is tert-butyl group, acetonide form may be produced via a 1,3-diol derivative in the same manner as in the above-mentioned, as shown in the following Scheme 10.

[Scheme 10]

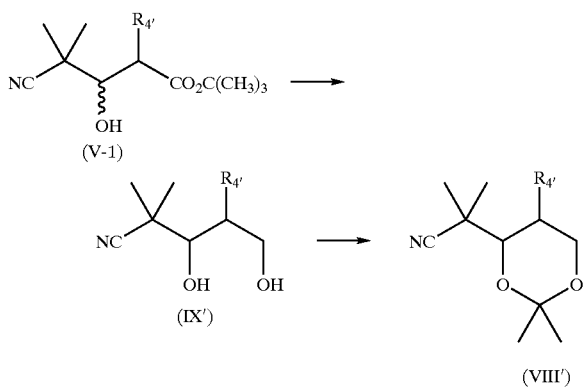

In the above-mentioned Scheme, $R_{4'}$ is as defined above.

The acetonide form of the above-mentioned formula (VIII'), which is obtained in this way, is considered to be useful as a synthetic intermediate for an epothilone derivative.

The present invention is described in more detail in the following by means of Examples and Reference Examples, which are not to be construed as limitative.

REFERENCE EXAMPLE 1

Synthesis of Ethyl 2,2-dimethylcyanoacetate

In a 2 L four-necked flask, ethyl cyanoacetate (250.0 g, 2.210 mol) and dimethyl sulfate (613.3 g, 4.862 mol) were simultaneously added dropwise to a solution of 60% sodium hydride (203.3 g, NaH=5.083 mol) in THF (1050 mL) at 35–45° C. over 4 hr 55 min. After the completion of the reaction, the reaction mixture was added to an aqueous acetic acid solution containing acetic acid (79.7 g, 1.3 mol) and water (545 mL), and the mixture was maintained at 65–70° C. for 2 hr to decompose remaining dimethyl sulfate. The reaction mixture was cooled to room temperature and adjusted to pH 6.80–7.50 with 20.5% NaOH (172.6 g). The THF layer was separated and THF was evaporated under somewhat reduced pressure (20–26.6 kPa) and then distilled under reduced pressure of 1.3–1.6 kPa. As a result, ethyl 2,2-dimethylcyanoacetate (270.4 g) was obtained as a fraction at 62–69° C. The yield was 86.7% relative to ethyl cyanoacetate.

EXAMPLE 1

Synthesis of tert-butyl 4-cyano-4-methyl-3-oxopentanoate

In a 500 mL four-necked flask under a nitrogen atmosphere, were charged dry THF (150 mL), ethyl 2,2-dimethylcyanoacetate (141 g, 1.0 mol) and tert-butyl acetate (141.5 g, 1.05 mol), and the mixture was cooled to −70° C. Thereto was dropwise added 2 M lithium diisopropylamide (1.00 mol)/heptane-THF solution (500 mL) over 6 hr while maintaining the mixture at −80° C. to −60° C.

After the completion of the dropwise addition, the reaction mixture was stirred at the same temperature for about 1 hr. The reaction mixture was warmed to room temperature (10–30° C.) and 2 M aqueous hydrochloric acid solution (608 g) was added dropwise thereto to adjust the pH to 7–7.5. By partitioning, the organic layer was obtained, which was concentrated under reduced pressure to give tert-butyl 4-cyano-4-methyl-3-oxopentanoate as an orange-brown oil (211 g). The yield was 100% relative to ethyl 2,2-dimethylcyanoacetate.

$^1$H-NMR(CDCl$_3$)(δppm): 1.49 (9H, s), 1.55 (6H, s), 3.72 (2H, s).

EXAMPLE 2

Synthesis of tert-butyl 4-cyano-3-hydroxy-4-methylpentanoate

In a 300 mL four-necked flask were charged dry THF (105 mL) and tert-butyl 4-cyano-4-methyl-3-oxopentanoate (30.07 g, 0.142 mol), and sodium borohydride (3.24 g, 0.0854 mol) was added. The reaction mass was stirred at room temperature for 2 hr and disappearance of the starting material was confirmed by thin-layer chromatography (TLC). After the confirmation, the reaction mixture was used as it was in Example 3.

EXAMPLE 3

Synthesis of 4-cyano-3-hydroxy-4-methylpentanoic Acid

To the reaction mixture obtained in Example 2 were added 10% aqueous sodium hydroxide solution (113.8 g) and methanol (20 mL), and the mixture was stirred at room temperature overnight. The disappearance of tert-butyl 4-cyano-3-hydroxy-4-methylpentanoate was confirmed by gas chromatography (GC). Toluene (50 mL) was added and the mixture was stirred and then partitioned to remove the toluene layer. 20% Aqueous hydrochloric acid solution (67.5 g) was added to the aqueous layer to adjust its pH to an acidic one (ca. pH 1–2) and the mixture was extracted twice with ethyl acetate (150 mL). The ethyl acetate layer was concentrated under reduced pressure to give 4-cyano-3-hydroxy-4-methylpentanoic acid (19.9 g) as an oil. When left standing, this oil crystallized. The yield was 89% relative to tert-butyl 4-cyano-3-hydroxy-4-methylpentanoate.

EXAMPLE 4
Synthesis of 4-cyano-3-hydroxy-4-methylpentanoic Acid

To the reaction mixture obtained by the method of Example 2 were added 10% aqueous sodium hydroxide solution (113.8 g) and methanol (20 mL), and the mixture was stirred overnight at room temperature. The disappearance of tert-butyl 4-cyano-3-hydroxy-4-methylpentanoate was confirmed by GC. Toluene (50 mL) was added, and the mixture was stirred and then partitioned to remove the toluene layer. 20% Aqueous hydrochloric acid solution (67.5 g) was added to the aqueous layer to adjust its pH to an acidic one (ca. 1–2), and the mixture was extracted twice with a mixed solution (150 mL) of ethyl acetate-n-butanol (1:1). The layer of the mixed solution was concentrated under reduced pressure to give 4-cyano-3-hydroxy-4-methylpentanoic acid (18.75 g) as an oil. The yield was 84% relative to tert-butyl 4-cyano-3-hydroxy-4-methylpentanoate, but crystallization did not occur.

REFERENCE EXAMPLE 2
Synthesis of R-N-(p-hydroxybenzyl)phenylethylamine (R-HBPEA)

Methanol (97 mL) and p-hydroxybenzaldehyde (25.65 g, 0.21 mol) were added, and R-(+)-phenylethylamine (24.24 g, 0.20 mol) was added thereto. The temperature of the mixture was raised to about 50° C. and, after the addition of the seed crystals, the reaction mixture was gradually cooled to precipitate crystals of a benzylidyne form. To this slurry was dropwise added a solution of sodium borohydride (4.55 g, 0.20 mol) in 0.05 N sodium hydroxide/water (10 mL) at 20–25° C. The reaction mass was stirred at the same temperature for 2 hr and concentrated to remove methanol. To the concentrate were added toluene (160 mL) and water (80 mL) and the mixture was stirred. The pH was adjusted to 7.8–8.2 with 12% aqueous hydrochloric acid solution, and an aqueous layer was removed. The toluene layer was washed with water (80 mL) and dried over anhydrous magnesium sulfate. Toluene was removed by concentration under reduced pressure to give R-HBPEA (47.7 g).

EXAMPLE 5
Optical Resolution of 4-cyano-3-hydroxy-4-methylpentanoic Acid
(1) Crystallization 4-Cyano-3-hydroxy-4-methylpentanoic acid (10.0 g, 63.63 mmol) was dissolved in ethyl acetate (180 mL) and R-HBPEA (14.46 g, 63.63 mmol) was added thereto and dissolved. The mixture was stirred for some time, during which a salt precipitated out. The temperature of the mixture was raised to 66.5° C. and methanol was added until the salt was dissolved. The amount of methanol added then was 40 mL. This solution was stirred under reflux for about 15 min and then cooled. At around 55° C., the salt precipitated out. The mixture was stirred at the same temperature for about 30 min, after which gradually cooled to 25° C. The mixture was stirred at this temperature for about 30 min and filtrated. The filtrate was washed with a mixed solvent (20 mL) of ethyl acetate:methanol=6:1 (v/v). The obtained white crystals of the salt were dried to give 5.61 g (yield: 22.94%) thereof. The optical purity was 89.78% e.e.

(2) Recrystallization

The salt (5.43 g, 14.12 mmol) obtained by crystallization of the above-mentioned (1) and ethyl acetate (37.8 mL) were added. The temperature of the mixture was raised to 60° C. and methanol was added until the salt was dissolved. The amount of methanol added then was 18.2 mL and the dissolution temperature was 61° C. When this solution was cooled, it became a suspension at around 59° C. Thus, the mixture was stirred at this temperature for about 30 min. Thereafter, the mixture was gradually cooled to 25° C. (10° C./hr) and stirred at this temperature for about 30 min. The salt was collected by filtration, washed with a mixed solvent (10 mL) of ethyl acetate:methanol=7:3 (v/v) and dried to give R-N-(p-hydroxybenzyl)phenylethylamine (R-HBPEA) salt (3.70 g) of optically active 4-cyano-3-hydroxy-4-methylpentanoic acid. The yield was 68.14% relative to the charged amount of the salt.

(3) Decomposition of Amine Salt

The R-HBPEA salt of the optically active 4-cyano-3-hydroxy-4-methylpentanoic acid obtained in the above-mentioned (2) was taken by 1 g and added to a solution of 2.6 ml of water, 310 mg of potassium hydroxide and 2.6 ml of toluene. After the addition, 10% hydrochloric acid was added while stirring the solution to make the pH of the aqueous layer 8.5–9. The mixture was stood at 40–50° C. and partitioned. Hydrochloric acid was further added to the aqueous layer to make the pH 1–2. The mixture was extracted with ethyl acetate and concentrated to give optically active 4-cyano-3-hydroxy-4-methylpentanoic acid.

The thus-obtained optically active 4-cyano-3-hydroxy-4-methylpentanoic acid was reacted with benzyl bromide in a DMF solvent using diisopropylethylamine as a base to convert the acid to benzyl ester, which was analyzed by liquid chromatography (LC). The optical purity was 99.2% e.e.

[LC Method]
Column: Chiral Cel OD (Daicel)
  4.6 mm$\phi$×25 cm
mobile phase:4% 2-propanol/hexane
flow:1.0 ml/min
RT (R form): 27.56 min
RT (S form): 19.60 min
  $^1$H-NMR(CDCl$_3$)($\delta$ppm): 1.37(3H, s, CH$_3$), 1.41(3H, s, CH$_3$), 2.60–2.67(1H, dd, C(H)H), 2.74–2.79(1H, dd, C(H)H), 3.97–4.0(1H, dd, CH).

EXAMPLE 6
Synthesis of Methyl 4-cyano-3-hydroxy-4-methylpentanoate

4-Cyano-3-hydroxy-4-methylpentanoic acid (7.7 g, 49 mmol) was dissolved in DMF (50 mL) and potassium carbonate (10.16 g, 73.5 mmol) was added. Dimethyl sulfate (8.03 g, 63.7 mmol) was dropwise added with vigorous stirring. The mixture was stirred at room temperature for 2 hr and toluene (50 mL) was added. 2N Aqueous hydrochloric acid solution (40 mL, 80 mmol) was dropwise added with vigorous stirring. After partitioning, a toluene layer was separated and an aqueous layer was extracted again with toluene (25 mL). The toluene layers were combined and concentrated under reduced pressure to give methyl 4-cyano-3-hydroxy-4-methylpentanoate (7.13 g, 41.6 mmol). The yield was 85% relative to 4-cyano-3-hydroxy-4-methylpentanoic acid.

$^1$H-NMR(CDCl$_3$)(δppm): 1.37–1.41 (6H, d), 2.55–2.75 (2H, m), 3.75 (3H, s), 3.92–3.96 (1H, dd).

EXAMPLE 7
Synthesis of Optically Active Methyl 4-cyano-3-hydroxy-4-methylpentanoate R-N-(p-Hydroxybenzyl)phenylethylamine salt (8.42 g, 22.7 mmol) of optically active 4-cyano-3-hydroxy-4-methylpentanoic acid was dissolved in water (20 mL) and toluene (20 mL) was added. 2N Aqueous potassium carbonate solution (22.7 mL, 45.4 mmol) was gradually added dropwise with vigorous stirring. After stirring vigorously at room temperature for 30 min, the mixture was partitioned and an organic layer was removed. Then, toluene (20 mL) and tetrabutylammonium bromide (1.01 g, 3.42 mmol) were added and dimethyl sulfate (3.15 g, 25.0 mmol) was dropwise added with vigorous stirring. The reaction mixture was stirred at room temperature for 2 hr, and a toluene layer was separated and concentrated under reduced pressure to give optically active methyl 4-cyano-3-hydroxy-4-methylpentanoate (3.62 g). The yield was 93.4% relative to optically active 4-cyano-3-hydroxy-4-methylpentanoic acid.

$^1$H-NMR(CDCl$_3$)(δppm): 1.37–1.41 (6H, d), 2.55–2.75 (2H, m), 3.75 (3H, s), 3.92–3.96 (1H, dd).

EXAMPLE 8
Synthesis of Optically Active 1,3-diol Derivative from Optically Active β-hydroxy Acid Ester Optically active methyl 4-cyano-3-hydroxy-4-methylpentanoate (2 g, 11.7 mmol) was dissolved in THF (10 mL) and methanol (5 mL) was added. An aqueous sodium borohydride (885 mg, 23.4 mmol) solution (5 mL) was dropwise added at room temperature. The mixture was stirred at room temperature for 3 hr and then 2N aqueous hydrochloric acid solution (15 mL) was dropwise added at 0° C. Ethyl acetate (20 mL) was added and the mixture was stirred vigorously. An organic layer was extracted. Ethyl acetate (20 mL) was further added to the aqueous layer and the mixture was stirred vigorously. The organic layer was extracted again. This step was repeated three times and the obtained organic layer was dried over anhydrous magnesium sulfate (2 g) and concentrated under reduced pressure to give optically active 4-cyano-4-methyl-3-hydroxy-1-pentanol (1.12 g, 7.84 mmol) (yield relative to optically active methyl 4-cyano-3-hydroxy-4-methylpentanoate: 67%).

The obtained optically active 4-cyano-4-methyl-3-hydroxy-1-pentanol was reacted with benzoyl chloride in a pyridine solvent using 4-dimethylaminopyridine as a catalyst, thereby converting to dibenzoate, which was analyzed by liquid chromatography (LC). The optical purity was 99.49% e.e.

[LC Method]
Column:Chiral Cel OD (Daicel)
  4.6 mmφ×25 cm
mobile phase:2% 2-propanol/hexane
flow:0.5 ml/min
RT (R form): 38.49 min
RT (S form): 41.75 min $^1$H-NMR(CDCl$_3$)(δppm): 1.40–1.44 (6H, d), 1.54–1.82 (2H, m), 3.67–3.71 (1H, dd), 3.81–4.05 (2H, m).

EXAMPLE 9
Synthesis of Optically Active 1,3-diol Derivative from Optically Active β-hydroxy Acid Optically active 4-cyano-3-hydroxy-4-methylpentanoic acid (1.5 g, 9.54 mmol) was dissolved in dry THF (5 mL) and a solution (38.175 mmol) of borane-THF complex was gradually added dropwise thereto at 0° C. After the completion of the dropwise addition, the mixture was stirred at room temperature for 3 hr and then 2N aqueous hydrochloric acid solution was added to neutralize the reaction mixture. Ethyl acetate (20 mL) was added thereto and the mixture was stirred vigorously. An organic layer was extracted. Ethyl acetate (20 mL) was further added to an aqueous layer and the mixture was stirred vigorously. The organic layer was extracted again. This step was repeated 3 times and the obtained organic layer was dried over anhydrous magnesium sulfate and concentrated under reduced pressure to give optically active 4-cyano-4-methyl-3-hydroxy-1-pentanol (847 mg, 5.915 mmol) (yield relative to optically active 4-cyano-3-hydroxy-4-methylpentanoic acid: 62%).

The obtained optically active 4-cyano-4-methyl-3-hydroxy-1-pentanol was analyzed in the same manner as in Example 8.

EXAMPLE 10
Synthesis of Optically Active 4-(1-cyano-1-methylethyl)-2,2-dimethyl-1,3-dioxane (Acetonide Form of a 1,3-diol Derivative)

Optically active 4-cyano-4-methyl-3-hydroxy-1-pentanol (500 mg, 3.49 mmol) was dissolved in 2,2-dimethoxypropane (5 mL) and p-toluenesulfonic acid (50 mg) was added. The mixture was stirred at room temperature for 30 min. Thereto was added a powder of potassium carbonate (100 mg) to neutralize the reaction mixture. The mixture was filtrated and concentrated under reduced pressure to give optically active 4-(1-cyano-1-methylethyl)-2,2-dimethyl-1,3-dioxane (614 mg, 3.35 mmol) (yield relative to optically active 4-cyano-4-methyl-3-hydroxy-1-pentanol: 96%).

The obtained optically active 4-(1-cyano-1-methylethyl)-2,2-dimethyl-1,3-dioxane was analyzed by gas chromatography (GC). The optical purity was 99.44% e.e.

| [GC Method] | |
| --- | --- |
| Column | Chirasil-Dex (Manuf. Chrompack) |
| Length | 50 m |
| ID | 0.25 mm |
| Film | 0.25 μm |
| Detector | FID |
| Injection Temp. | 250° C. |
| Detectors Temp. | 280° C. |
| Column Temp. | 80° C. (isotherm) |
| Gas | H$_2$, 75 kPa |
| RT (R form) | 12.85 min |
| RT (S form) | 13.27 min |

$^1$H-NMR(CDCl$_3$)(δppm): 1.31–1.35 (6H, d), 1.40–1.44 (6H, d), 1.54–1.82 (2H, m), 3.67–3.71 (1H, dd), 3.91–3.97 (2H, m).

EXAMPLE 11
Synthesis of Optically Active 4-(1-cyano-1-methylethyl)-2,2-dimethyl-1,3-dioxane(an Acetonide Form of a 1,3-diol Derivative)

Optically active 4-cyano-4-methyl-3-hydroxy-1-pentanol (500 mg) was dissolved in acetone (5 mL) and p-toluenesulfonic acid (50 mg) and powder molecular sieve 4A (100 mg) were added. The mixture was stirred at room temperature for 1 hr. Thereto was added a powder of potassium carbonate to neutralize the reaction mixture, which was filtrated and concentrated under reduced pressure to give optically active 4-(1-cyano-1-methylethyl)-2,2-dimethyl-1,3-dioxane.

The obtained optically active 4-(1-cyano-1-methylethyl)-2,2-dimethyl-1,3-dioxane was analyzed in the same manner as in Example 10.

$^1$H-NMR(CDCl$_3$)(δppm): 1.31–1.35 (6H, d), 1.40–1.44 (6H, d), 1.54–1.82 (2H, m), 3.67–3.71 (1H, dd), 3.91–3.97 (2H, m).

EXAMPLE 12

Synthesis of tert-butyl 4-cyano-2,4-dimethyl-3-oxopentanoate

A mixed solution of tert-butyl propionate (2.60 g, 20 mmol) and ethyl 2,2-dimethylcyanoacetate (2.82 g, 20 mmol) in dry THF (50 mL) was cooled to −70° C. and LDA (22 mmol) was dropwise added to this solution over 1 hr in such a manner that the internal temperature does not exceed −65° C. As the LDA, used was one prepared by diluting diisopropylamine (3.08 mL, 22 mmol) with dry THF (50 mL), cooling the solution to −50° C., dropwise adding n-BuLi (15% hexane solution) (9.365 g, 22 mmol), gradually raising the temperature to 0° C. and stirring for 30 min.

After dropwise addition of LDA, the mixture was stirred at −70° C. to −65° C. for 1 hr, after which it was gradually warmed to 0° C. over 0.5 hr. 1N Aqueous acetic acid solution (53 mL) was added to adjust pH to around 7 and the mixture was further stirred for 30 min.

The mixture was heated to 23° C. and toluene (50 mL) was added and stirred for 10 min. Partitioning gave an organic layer. This organic layer was washed with saturated brine (50 mL) and anhydrous magnesium sulfate (5 g) was added for drying.

Magnesium sulfate was removed by filtration and the filtrate was concentrated under reduced pressure to give tert-butyl 4-cyano-2,4-dimethyl-3-oxopentanoate (4.17 g, 18.51 mmol, yield: 92.5%).

$^1$H-NMR(CDCl$_3$)(δppm): 1.39–1.41 (d, J=17 Hz, 3H), 1.47 (s, 9H), 1.51 (s, 3H), 1.59(s, 3H), 4.05–4.10 (q, J=17 Hz, 1H).

TLC: Rf=0.40 (Heptane: AcOEt=4:1).

Example 13

Synthesis of tert-butyl 4-cyano-2,4-dimethyl-3-hydroxypentanoate tert-Butyl 4-cyano-2,4-dimethyl-3-oxopentanoate (400 mg, 1.775 mmol) obtained in Example 12 was diluted with methanol (5 mL) and cooled to 0° C. Sodium borohydride (20 mg, 0.53 mmol) was added. The mixture was stirred at 0° C. for 10 min and 10% aqueous hydrochloric acid solution (0.5 mL) was added. The mixture was further stirred for 10 min. Aqueous saturated sodium hydrogencarbonate solution (2 mL) was added and the mixture was further stirred for 10 min.

The temperature of the mixture was raised to 23° C. and concentrated under reduced pressure to remove methanol. Toluene (10 mL) was added to the concentrate, and the mixture was stirred for 10 min. Partitioning gave an organic layer. This organic layer was washed with saturated brine (5 mL) and anhydrous magnesium sulfate (1 g) was added for drying.

Magnesium sulfate was removed by filtration and the filtrate was concentrated under reduced pressure to give tert-butyl 4-cyano-2,4-dimethyl-3-hydroxy pentanoate (370 mg, 1.628 mmol, yield: 91.7%).

EXAMPLE 14

Synthesis of tert-butyl 4-cyano-2,4-dimethyl-3-hydroxypentanoate tert-Butyl 4-cyano-2,4-dimethyl-3-oxopentanoate (400 mg, 1.775 mmol) obtained in Example 12 was diluted with methanol (5 mL). Calcium chloride (394 mg, 3.55 mmol) was added at 30° C. and the mixture was stirred as it was for 30 min. The obtained transparent liquid was cooled to 0° C. and sodium borohydride (20 mg, 0.53 mmol) was added. The mixture was stirred at 0° C. for 10 min and 10% aqueous hydrochloric acid solution (0.5 mL) was added. The mixture was further stirred for 10 min and saturated aqueous sodium hydrogencarbonate solution (2 mL) was added. The mixture was further stirred for 10 min.

The temperature of the mixture was raised to 23° C. and concentrated under reduced pressure to remove methanol. Toluene (10 mL) was added to the concentrate, and the mixture was stirred for 10 min. Partitioning gave an organic layer. This organic layer was washed with saturated brine (5 mL) and anhydrous magnesium sulfate (1 g) was added for drying.

Magnesium sulfate was removed by filtration and the filtrate was concentrated under reduced pressure to give tert-butyl 4-cyano-2,4-dimethyl-3-hydroxypentanoate (374 mg, 1.645 mmol, yield: 92.7%).

EXAMPLE 15

Synthesis of tert-butyl 4-cyano-2,4-dimethyl-3-hydroxypentanoate tert-Butyl 4-cyano-2,4-dimethyl-3-oxopentanoate (400 mg, 1.775 mmol) obtained in Example 12 was diluted with methanol (5 L) and manganese(II) chloride (447 mg, 3.55 mmol) was added at 30° C. The mixture was stirred as it was for 30 min. The obtained transparent liquid was cooled to 0° C. and sodium borohydride (20 mg, 0.53 mmol) was added. The mixture was stirred at 0° C. for 10 min and 10% aqueous hydrochloric acid solution (0.5 mL) was added. The mixture was further stirred for 10 min and saturated aqueous sodium hydrogencarbonate solution (2 mL) was added. The mixture was further stirred for 10 min.

The temperature of the mixture was raised to 23° C. and concentrated under reduced pressure to remove methanol. Toluene (10 mL) was added to the concentrate, and the mixture was stirred for 10 min. Partitioning gave an organic layer. This organic layer was washed with saturated brine (5 mL) and anhydrous magnesium sulfate (1 g) was added for drying.

Magnesium sulfate was removed by filtration and the filtrate was concentrated under reduced pressure to give tert-butyl 4-cyano-2,4-dimethyl-3-hydroxypentanoate (366 mg, 1.61 mmol, yield: 90.7%).

The tert-butyl 4-cyano-2,4-dimethyl-3-hydroxypentanoates obtained in Examples 13–15 were examined for ratio of stereoisomers by $^1$H-NMR and HPLC, the results of which are shown in Table 1.

TABLE 1

| | Example 13 | Example 14 | Example 15 |
|---|---|---|---|
| Threo:Erythro ($^1$H-NMR) | 90.4:9.6 | 43.2:56.8 | 64.1:35.9 |
| Threo:Erythro (HPLC) | 91.9:8.1 | 46.7:53.3 | 68.8:31.2 |

[Threo Form]
$^1$H-NMR(CDCl$_3$)($\delta$ppm): 1.33 (s, 3H), 1.39 (s, 3H), 1.40–1.42 (d, J=18 Hz, 3H), 1.48 (s, 9H), 2.72–2.78 (dq, J=5.18 Hz, 1H), 3.44–3.47 (dd, J=5, 22 Hz, 1H), 4.68–4.70 (d, J=22 Hz, 1H).

TLC: Rf=0.35 (Heptane: AcOEt=4:1).

HPLC:[retention time] 7.12 min, 8.05 min (Daicel Chiral OD-H, Hexane:2-propanol=98:2, Flow 0.8 ml/min, Oven temp. 35° C.).

[Erythro Form]
$^1$H-NMR(CDCl$_3$)($\delta$ppm): 1.33(s, 6H), 1.34–1.36 (d, J=18 Hz, 3H), 1.46 (s, 9H), 2.67–2.74 (dq, J=8.18 Hz, 1H), 3.12–3.14 (d, J=10 Hz, 1H), 3.75–3.77 (dd, J=8.10 Hz, 1H).

TLC: Rf=0.30 (Heptane:AcOEt=4:1).

HPLC:[retention time] 11 min, 59 min (Daicel Chiral OD-H, Hexane:2-propanol=98:2, Flow 0.8 ml/min, Oven temp. 35° C.).

As is clear from the foregoing explanation, the present invention provides a compound useful as an intermediate for the synthesis of a pharmaceutical agent, an agrichemical agent and the like, particularly a novel synthetic intermediate for the synthesis of epothilone useful as an anticancer agent and derivatives thereof, and production methods thereof.

This application is based on a patent application Nos. 2001-304278, 2001-305854, 2001-306842 and 2002-62022 filed in Japan, the contents of which are hereby incorporated by reference.

What is claimed is:

1. A β-keto ester compound represented by the following formula

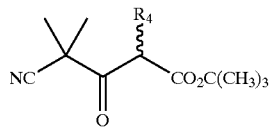

(I)

wherein R$_4$ is hydrogen atom or alkyl group having 1 to 6 carbon atoms, or an optically active form thereof.

2. The compound of claim 1, wherein R$_4$ is hydrogen atom, or an optically active form thereof.

3. The compound of claim 1, wherein R$_4$ is alkyl group having 1 to 6 carbon atoms, or an optically active form thereof.

4. A production method of a β-keto ester compound claim 1, which comprises condensation of a 2-cyano-2,2- dimethylacetate represented by the following formula

(II)

wherein R$_1$ is alkyl group having 1 to 6 carbon atoms, with an alkyl ester represented by the following formula

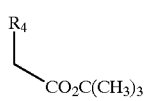

(III)

wherein R$_4$ is hydrogen atom or alkyl group having 1 to 6 carbon atoms, is the presence of a strong base.

5. The production method of claim 4, wherein R$_4$ is hydrogen atom.

6. The production method of claim 4, wherein R$_4$ is alkyl group having 1 to 6 carbon atoms.

7. The production method of claim 4, comprising adding lithium diisopropylamide as a strong base to a mixture of 2-cyano-2,2- dimethylacetate represented by the formula (II) and an alkyl ester represented by the formula (III).

8. The production of claim 4, which comprises adding cyanoacetate of the following formula

(IV)

wherein R$_1$ is alkyl group having 1 to 6 carbon atoms, and dimethyl sulfate continuously or discontinuously to a sodium hydride-containing tetrahydrofuran solution to give 2-cyano-2, 2-dimethylacelate of the formula (II), and condensation thereof with an alkyl ester of the formula (III).

9. A β-hydroxy acid compound represented by the following formula

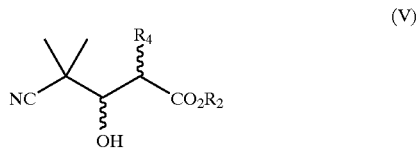

(V)

wherein R$_2$ is hydrogen atom or alkyl group having 1 to 6 carbon atoms, and R$_4$ is hydrogen atom or alkyl group having 1 to 6 carbon atoms, provided that when R$_4$, is alkyl group having 1 to 6 carbon atoms, R$_2$ should be tert-butyl-group, an optically active form thereof or a salt thereof.

10. The compound of claim 9, wherein R$_4$, is hydrogen atom, an optically active form thereof or a salt thereof.

11. The compound of claim 9, wherein R$_4$ is alkyl group having 1 to 6 carbon atoms and R$_2$ is tert-butyl group, an optically active form thereof or a salt thereof.

12. A production method of a β-hydroxy acid compound represented by the formula (V) of claim 9, which comprises reducing a β-keto ester compound represented by the following formula

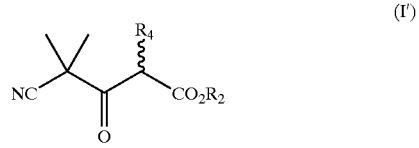

(I')

wherein R$_2$ is hydrogen atom or alkyl group having 1 to 6 carbon atoms, and R$_4$ is hydrogen atom or alkyl group having 1 to 6 carbon atoms, provided that when R$_2$ is alkyl group having 1 to 6 carbon atoms, R$_2$ should be tert-butyl group, or a salt thereof.

13. The production method of claim 12, wherein $_{R4}$, is alkyl group having 1 to 6 carbon atoms and R$_2$ is tert-butyl group.

14. The production method of claim 13, wherein the reduction is carried out using alkali borohydride and divalent metal chloride.

15. The production method of claim 12, wherein R$_2$, is hydrogen atom.

16. The production method of claim 15, wherein R$_2$ is alkyl group having 1 to 6 carbon atoms.

17. The production method of claim 16 wherein the alkyl group having 1 to 6 carbon atoms is tert-butyl group.

18. The production method of claim 15, wherein the reduction carried out using sodium borohydride.

19. The production method of claim 14, wherein the β-keto ester compound of the formula (I'), wherein $R_2$ is alkyl group having 1 to 6 carbon atoms and $R_4$ is hydrogen atom, is reduced to give a β-hydroxy acid compound (V-4) represented by the following formula

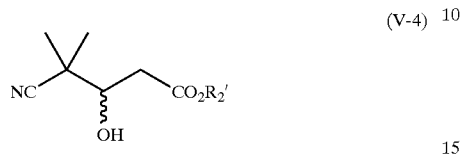
(V-4)

wherein $R_2$, is alkyl group having 1 to 6 carbon atoms, which is a compound of the formula (V) wherein $R_2$ is alkyl group having 1 to 6 carbon atoms and $R_4$ is hydrogen atom, and the p-hydroxy acid compound (V-4) is subjected to alkali hydrolysis to give a β-hydroxy acid compound (V-5) of the following formula

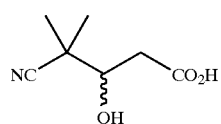
(V-5)

which is a compound of the formula (V) wherein $R_2$ and $R_4$ are hydrogen atoms.

20. The production method of claim 19, wherein the resulting β-hydroxy acid compound (V-5) is optically resolved to give a βhydroxy acid compound (V-6) of the following formula

(V-6)

or a salt thereof, which is then esterified with an alkylating agent to give a β-hydroxy acid compound (V-7) represented by the following formula

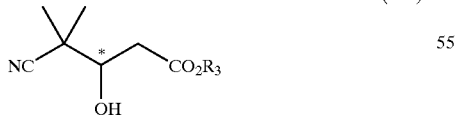
(V-7)

wherein $R_3$ is alkyl group having 1 to 6 carbon atoms, which is an optically active compound of the formula (V) wherein $R_2$ is alkyl group having 1 to 6 carbon atoms and $R_4$ is hydrogen atom.

21. The production method of claim 19, wherein each alkyl group having 1 to 6 carbon atoms is tert-butyl group.

22. A production method of a β-hydroxy acid compound (V-6) represented by the following formula

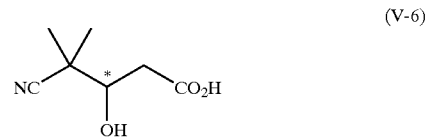
(V-6)

or a salt thereof, which is an optically active compound represented by the formula (V) of claim 9, wherein $R_2$ and $R_4$ are hydrogen atoms, which comprises optically resolution of the β-hydroxy acid compound (V-5) represented by the following formula

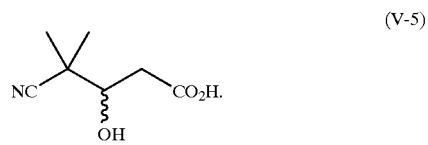
(V-5)

23. The production method of claim 22, wherein the βhydroxy acid compound (V-5) is converted to a salt with an optically active amine compound and optically resolved.

24. A production method of a β-hydroxy acid compound (V-7) represented by the following formula

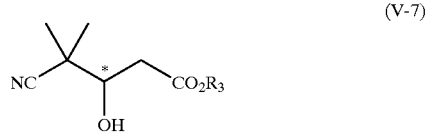
(V-7)

wherein $R_3$ is alkyl group having 1 to 6 carbon atoms, which is an optically active compound represented by the formula (V) of claim 9, wherein $R_2$ is alkyl group having 1 to 6 carbon atoms and $R_4$ is hydrogen atom, which comprises esterification of a β-hydroxy acid compound (V-6) represented by the following formula

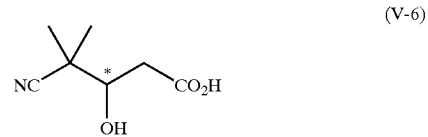
(V-6)

or a salt thereof with an alkylating agent.

25. An acetonide form of a 1,3-dial derivative, which is represented by the following formula

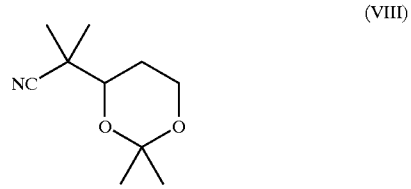
(VIII)

or an optically active form thereof.

26. A production method of an acetonide form of a 1,3-dial derivative represented by the formula (VIII) of claim 25, or an optically active form thereof, which com prises conversion of a 1,3-diol derivative represented by the following formula

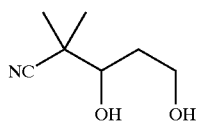
(VII)

or an optically active form thereof, to an acetonide form thereof.

27. The production method of claim 26, wherein the β-hydroxy acid compound of the following formula

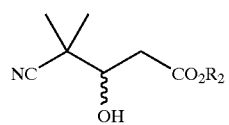
(V-2)

wherein $R_2$ is hydrogen atom or alkyl group having 1 to 6 carbon atoms, or an optically active form thereof is reduced to give a 1,3-diol derivative of the formula (VII) or an optically active form thereof, which is converted to an acetonide form.

28. A production method of a 1,3-diol derivative represented by the following formula

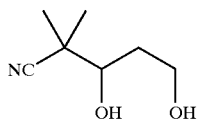
(VII)

or an optically active form thereof, which comprises reducing a β-hydroxy acid compound represented by the following formula

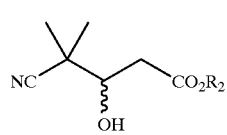
(V-2)

wherein $R_2$ is hydrogen atom or alkyl group having 1 to 6 carbon atoms, or an optically active form thereof.

* * * * *

UNITED STATES PATENT AND TRADEMARK OFFICE
CERTIFICATE OF CORRECTION

PATENT NO. : 6,730,803 B2
DATED : May 4, 2004
INVENTOR(S) : Iwasaki et al.

It is certified that error appears in the above-identified patent and that said Letters Patent is hereby corrected as shown below:

Title page,
Item [75], Inventors, "Hideto Miyamoto" should read -- Hidehito Miyamoto --.
Item [56], References Cited, FOREIGN PATENT DOCUMENTS,
"WO    WO 03/014063 A2    2/2003" should read as -- WO    03/014063 A2    02/2003 --.
"WO    WO 03/014068 A1    2/2003" should read as -- WO    03/014068 A1    02/2003 --.

Column 35,
Lines 47-48, "2-cyano-2,2- dimethylacetate" should read -- 2-cyano-2,2-dimethylacetate --.

Column 36,
Line 5, "2-cyano-2,2- dimethylacetate" should read -- 2-cyano-2,2-dimethylacetate --.
Line 53, "$R_2$" should read -- $R_4$ --.
Line 56, "$_{R4}$, is" should read -- $R_4$ is --.
Line 62, "$R_2$, is" should read -- $R_4$ is --.
Line 66, "16 wherein" should read -- 16, wherein --.

Column 37,
Line 20, "p-hydroxy" should read -- β-hydroxy --.
Line 37, "βhydroxy" should read -- β-hydroxy --.

Column 38,
Line 13, "optically" should read -- optical --.
Line 25, "βhydroxy" should read -- β-hydroxy --.
Lines 52 and 66, "1,3-dial" should read -- 1,3-diol --.
Line 67, "com" should read -- com- --.

Signed and Sealed this

Fourteenth Day of December, 2004

JON W. DUDAS
*Director of the United States Patent and Trademark Office*

Disclaimer

6,730,803 B2—Mitsuhiro Iwasaki, Osaka (JP); Kiyoshi Sugi, Osaka (JP); Hideto Miyamoto, Osaka (JP); Nobushige Itaya, Osaka (JP). SYNTHETIC INTERMEDIATE FOR EPOTHILONE DERIVATIVE AND PRODUCTION METHOD THEREOF. Patent dated May 4, 2004. Disclaimer filed November 29, 2004 by Assignee, Sumitomo Chemical Company, Limited.

Hereby enters this disclaimer to claims 1, 2, 9, 10, 25 and 26 of said patent.

(*Official Gazette, September 20, 2005*)